United States Patent
Zours

(10) Patent No.: US 7,662,121 B2
(45) Date of Patent: Feb. 16, 2010

(54) SPINAL ORTHOTIC DEVICES

(76) Inventor: Claudia Zours, Hülsbergstrasse 12a, Busan (DE) 44797

( * ) Notice: Subject to any disclaimer, the term of this patent is extended or adjusted under 35 U.S.C. 154(b) by 295 days.

(21) Appl. No.: 11/685,730

(22) Filed: Mar. 13, 2007

(65) Prior Publication Data
US 2008/0045873 A1 Feb. 21, 2008

(30) Foreign Application Priority Data
Mar. 14, 2006 (DE) .................. 20 2006 004 190 U
Sep. 15, 2006 (DE) ...................... 10 2006 043 846

(51) Int. Cl.
*A61F 5/00* (2006.01)
(52) U.S. Cl. ....................... 602/19; 128/96.1
(58) Field of Classification Search ............... 602/5, 602/18, 19; 128/96.1, 100.1, 102.1, 106
See application file for complete search history.

(56) References Cited

U.S. PATENT DOCUMENTS

| 3,945,376 | A | * | 3/1976 | Kuehnegger | ................ | 602/19 |
| 4,508,110 | A | * | 4/1985 | Modglin | .................. | 602/19 |
| 5,765,224 | A | * | 6/1998 | Johnson | ............................. | 2/44 |
| 7,025,737 | B2 | * | 4/2006 | Modglin | ..................... | 602/19 |

FOREIGN PATENT DOCUMENTS

| DE | 103 29 454 | 1/2005 |
| GB | 740507 | 11/1953 |
| WO | PCT/RU99/00216 | 6/1999 |
| WO | PCT/EP03/02430 | 3/2003 |

OTHER PUBLICATIONS

European Search Report for European Application No. EP 07 10 4043.

* cited by examiner

*Primary Examiner*—Michael A. Brown
(74) *Attorney, Agent, or Firm*—Intellectual Property Law Group LLP; Juneko Jackson; Otto O. Lee

(57) ABSTRACT

The invention relates to a spinal orthotic device configured from one or more elements of a modular system, comprising the following elements:
  a lower abdominal corset (40, 120),
  an upper abdominal corset (17, 130) that can be attached cranially to the lower abdominal corset (40, 120),
  a corset supporting element (41) that can be secured posteriorly in the lower abdominal corset (40, 120) and is arranged along the lumbar spine, supporting the spine while restricting sagittal mobility,
  a thoracic spinal corset (10, 200) that can be attached cranially to the lower abdominal corset (40, 120),
  at least one curved supporting clasp (47) that can be inserted posteriorly optionally into a bandage of a lower abdominal corset (40, 120) and an upper abdominal corset (17, 130) or into an bandage of a lower abdominal corset (40, 120) and a thoracic spinal corset (10, 200), said curved supporting clasp being attached to a corset supporting element (41) for correction of lordosis and for restriction of sagittal and frontal mobility in the area of the lumbar spine,
  at least one supporting element (23, 160) which can optionally be secured cranially in the thoracic spinal corset (10, 200) and caudally to the corset supporting element (41, 150) and extends laterally along the spine to align and relieve the spine in the sagittal plane,
  and an abdominal truss pad (190) that can be attached ventrally to a lower abdominal corset (40, 120) for correction of lordosis of the lumbar spine and increasing the intra-abdominal pressure.

18 Claims, 26 Drawing Sheets

SPINAL ORTHOTIC DEVICES

BACKGROUND OF THE INVENTION

1. Field of Invention

The present invention relates to the field of spinal orthotic devices, which are configured as elements of a modular system.

Such a spinal orthotic device is known from Unexamined German Patent DE 103 29 454 A1, among others.

Various symptoms in the spinal area are treated with a variety of orthotic devices which support and/or align the spine in the affected portions and/or restrict its mobility in the various planes. The supporting behavior and the stiffness of the orthotic device are determined by the patient's progress in recovery. In the past, new orthotic devices would be prescribed repeatedly in the course of recovery so that their supporting behavior or rigidity would take into account the patient's indication as well as the patient's current progress in recovery.

To reduce costs for medical insurance carriers, modular systems for orthotic devices that can be adapted approximately to the area of the spine to be supported have been developed. An example of such a modular system is known from DE 103 29 454 A1.

However, the modular system known previously does not meet all the demands of flexibility and adaptability. For example, the known modular system does not allow optional support in the sagittal plane or simultaneous support in both sagittal and frontal planes. In addition, there are no provisions for adapting the rigidity of the support to the particular progress during recovery. Finally, the modular system known in the past does not allow fine adjustment of the orthotic device that is to be configured to the particular body size of the wearer in fine increments.

2. Summary of the Invention

Therefore, the object of the present invention is to provide a modular system for spinal orthotic devices such that its spinal orthotic devices can be adapted flexibly to a great extent to the particular symptoms and the patient's progress in recovery. With the smallest possible number of elements, the largest possible variety of orthotic devices should configurable so that they can be used with a variety of diseases and their supporting properties can be increased or decreased.

This object is achieved by a modular system having the technical features of Claim 1. The object for which patent protection is sought is such a spinal orthotic device that can be configured using this modular system, although the spinal orthotic device cannot make use of all elements of the modular system in principle.

The seven elements described in Claim 1 (see also a1) to c1), e1), g1), h1) and i1))—the lower abdominal corset (also known as a lumbar spinal corset), the upper abdominal corset (also known as a shoulder strap system), the corset supporting element (also known as a basic truss pad), the thoracic corset (also known as a thoracic orthotic or thoracic orthotic device), the curved supporting clasp on a corset supporting element, the supporting element and the abdominal truss pad—constitute the basic elements of the basic modular system from which the inventive orthotic devices can be configured. Some of the basic elements of the modular kit are needed for various orthotic devices and thus are reusable if the patient needs a different orthotic device. The modular system also allows therapeutically correct training of the spine, wherein elements are removed successively from a more complex orthotic device, which is thus dismantled incrementally. If there is a delay in recovery, it is possible at any time to return an orthotic device that has been removed too soon, to thereby return to a higher level of support.

The advantage of this fundamental modular system may be regarded as the fact that with a minimal number of elements, as listed in Claim 1, a wide variety of orthotic devices can be assembled for the particular application case. The respective orthotic devices can be adapted in a flexible manner to each patient's particular medical and physical needs with an accurate fit. Expedient embodiments of the first basic modular system of a spinal orthotic device are characterized in subordinate Claims 2 to 9.

The essential difference from the second basic exemplary embodiment according to the additional Claims 10 to 15 may be regarded as the fact that additional elements must be added to make the particular orthotic devices expandable among one another. For example, an additional connecting element is used in the second basic exemplary embodiment. Furthermore, the corset supporting elements are designed as truss pads (also called pelotte) in a complex manner. A basic truss pad (also called basic pelotte) is used as the corset supporting element in the second basic exemplary embodiment.

The nine elements described in Claim 10 (see a2) to i2))—the lower abdominal corset, the upper abdominal corset, the basic truss pad, the lumbar extension for the basic truss pad, the thoracic corset, the connecting element, the bridging frame, the supporting element and the abdominal truss pad—are the basic elements of the additional modular system with which at least seven different orthotic devices can be configured according to this invention. Some of the basic elements of the modular kit are needed for different orthotic devices and are thus reusable if the patient needs a different orthotic device. The modular system also allows therapeutically correct training in that elements are removed successively from a more complex orthotic device, which is therefore decreased incrementally. It is possible at any time to reassemble the orthotic device that has been removed too soon in the event of a delay in recovery in order to thereby return to a higher level of support.

Expediently a sectional truss pad, which is known per se, is selected as the basic truss pad, comprising four sections joined together in an articulated fashion and arranged along the lumbar spine, transversely bridging the third to fifth lumbar vertebra and the first sacral vertebra. Such a sectional truss pad has proven excellent in therapeutic practice in comparison with other truss pads.

Since the joints of the sectional truss pad usually also allow a certain mobility of the individual sections in relation to one another in the sagittal plane, it is advisable to provide a fixation element within the modular system, so that it can be placed in a posterior position on the sectional truss pad, so that the sections of the truss pad are secured immovably in relation to one another in the sagittal plane.

A suitable lumbar extension for a sectional truss pad comprises two sections that can be connected together in an articulated manner plus two supporting rails, where the sections of the lumbar extension can be inserted into the sectional truss pad in such a way that the sections of the sectional truss pad, which has been extended by the lumbar extension, bridge the first to fifth lumbar vertebrae as well as the first sacral vertebra transversely and the supporting rails can be placed laterally on the sectional truss pad in such a way that at least the sections bridging the first four lumbar vertebrae are secured immovably in relation to one another. The lumbar extension for a sectional truss pad is thus not attached to the existing sectional truss pad to also include vertebrae L1 and L2, but instead is inserted into the sectional truss pad, so that the section that was assigned to L3 in the basic configuration now bridges L1. One section of the lumbar extension is allocated to L2, while the other section of the lumbar extension continues to support L3.

To make the supporting rigidity of the bridging frame more adjustable, it is advisable to provide a tenth element in the form of reinforcing rods that can be secured on the bridging frame to adjust the rigidity.

Additional measures that improve the present invention are characterized in the subordinate claims or are presented below and explained in greater detail jointly with the description and the preferred exemplary embodiments of the invention on the basis of the figures. FIGS. 1 to 12 illustrate the first basic modular system for spinal orthotic devices. The additional FIGS. 13 to 28, however, additionally disclose the fundamental modular system for spinal orthotic devices:

DETAILED DESCRIPTION OF SPECIFIC EMBODIMENTS

Figure 1:
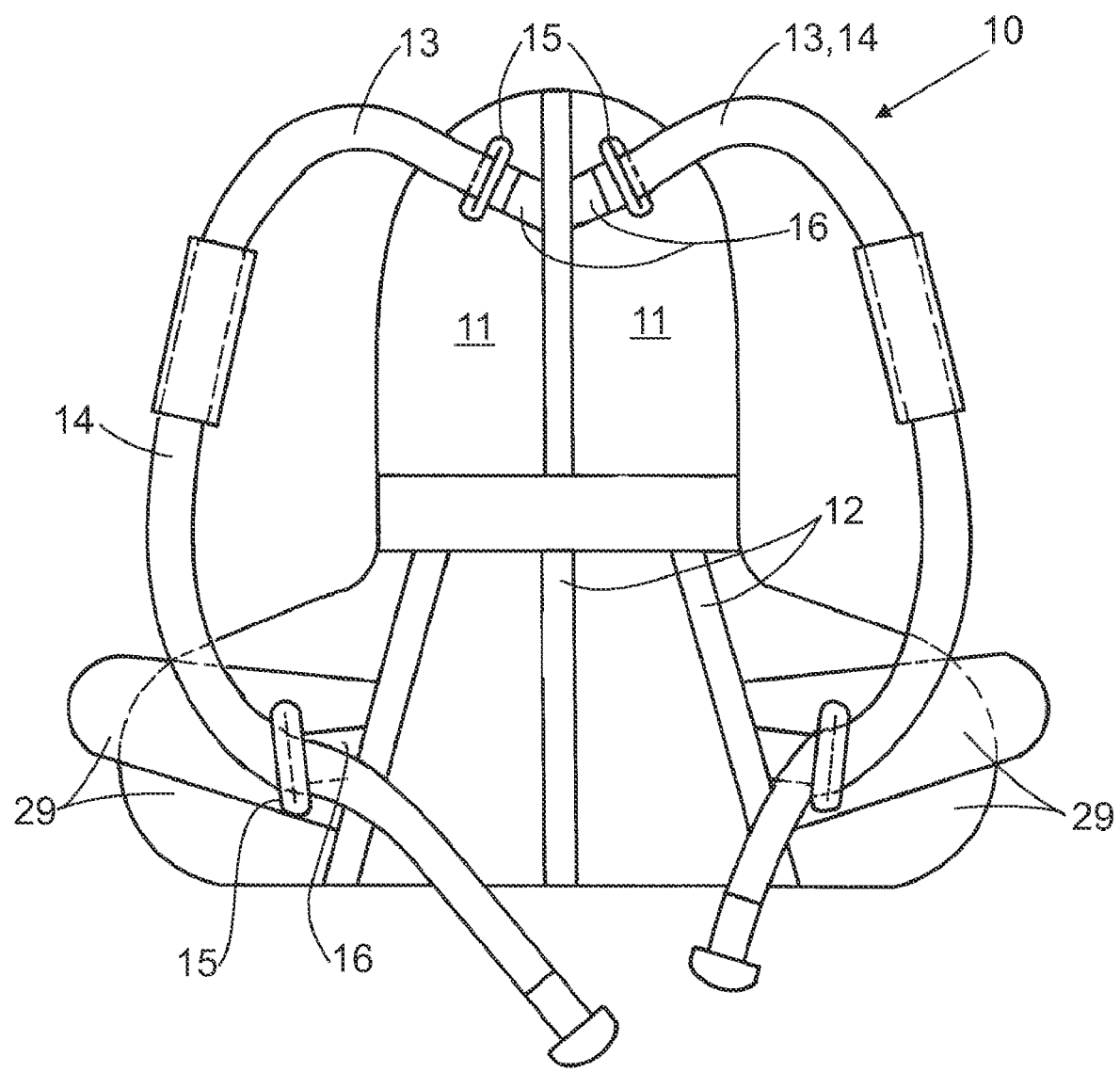
FIG. 1 shows a rear view of a first variant of an inventive thoracic vertebral orthesis without a shoulder strap system.

FIG. 1 shows an inventive thoracic spinal orthotic device 10, as seen in a view from the rear. The triangular posterior part 11 is shown with very rounded corners and also with stripes 12 in the form of cloth strips or parts of a hook-and-loop fastener (also called VELCRO-type closure parts). This posterior part 11 is designed to be in symmetry with the spine and/or a vertical line. On the cranial end of the posterior part 11 two inelastic belts 14 of the shoulder belt system 13 are arranged in the area of the spine. Belt holders 15 consisting essentially of a closed curved plastic part are used here. These belt holders 15 are attached to the posterior part 11 by elastic bands 16. The elastic bands 16 run diagonally away from the spine, with the bands arranged in an ascending pattern to the shoulder. The inelastic belts 14 of the shoulder belt system 13 are arranged on the belt holders 15. These run toward the lower belt holders 15 which are also arranged on the posterior part 11 via elastic bands 16. The lower belt holders 15 are arranged a greater distance away from the spine on the posterior part 11, so as not to leave too much clearance for the shoulder belt system 13 due to the elastic bands 16. Thus, only short elastic bands 16 are used and may be attached to the posterior part 11 by sewing or gluing. The caudal belt holders 15 have guide straps 35 which are shown separately in FIGS. 12*a* and 12*b*.

For ventral fastening of the thoracic spinal orthotic device 10, a shoulder strap system 17 is provided, including a belt 18 not shown in FIG. 1. This shoulder strap system 17 may be attached to the posterior part 11 by the double wall-fastening tabs 29 (shown in FIG. 1). To do so, the fastening tabs 29 are provided with corresponding VELCRO-type closure parts on the inside which cooperate with mating VELCRO-type closure parts on the belts 18 of the shoulder strap system 17. The belts 18 are arranged on the fastening tab 29 via the stationary belt ends 19. To shorten the belts 18 to the required length, it is possible to simply cut off the stationary belt ends 19 accordingly. The shoulder strap system 17 is closed ventrally with a VELCRO-type closure, for example, via the open belt ends 20. A supporting element 23 that is provided is arranged preferably on the side of the posterior part 11 facing the back and therefore is not visible in FIG. 1.

Figure 2:
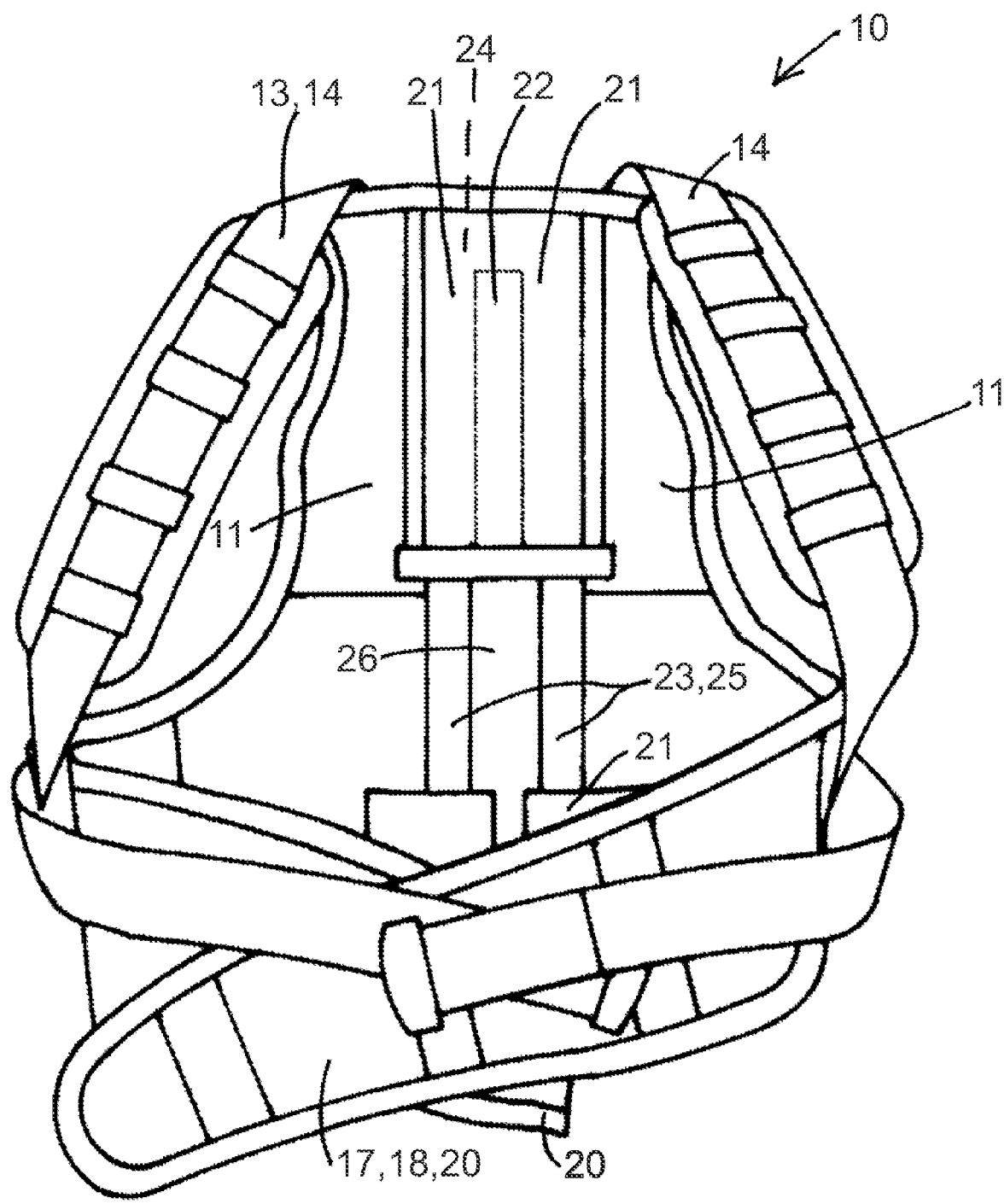
FIG. 2 shows a front view of another inventive variant of the thoracic vertebral orthesis with a shoulder strap system and a strap-like supporting element.

FIG. 2 shows another inventive thoracic spinal orthotic device 10. Supporting element 23 arranged inside the pocket 21 can be seen clearly here. This supporting element 23 is designed with a bow shape, in particular a U shape, but the U is upside down. The cranial end 24 of the supporting element 23 as well as the caudal ends 25 of the supporting element 23 are arranged in closable pockets 21. These pockets 21 can be closed by VELCRO-type closures 22 in the present case. With the thoracic spinal orthotic device 10 shown in FIG. 2, the shoulder strap system 17 is inseparably connected to the posterior part 11. Consequently, the fastening tabs 29 for holding the shoulder strap system 17, in particular the belt 18, are not used here. As can also be seen here, the supporting element 23 has a recess 26 between the two rod-like ends 25 to be able to accommodate the spine in this recess. This thoracic spinal orthotic device 10 is fully usable in the condition shown in FIG. 2. Other supporting elements 23 may of course also be used, e.g., secured in a stationary position on the posterior part 11 in the form of truss pads. It is also conceivable to reinforce these supporting elements 23 with additional reinforcing elements.

Figures 3A, 3B, 3C:
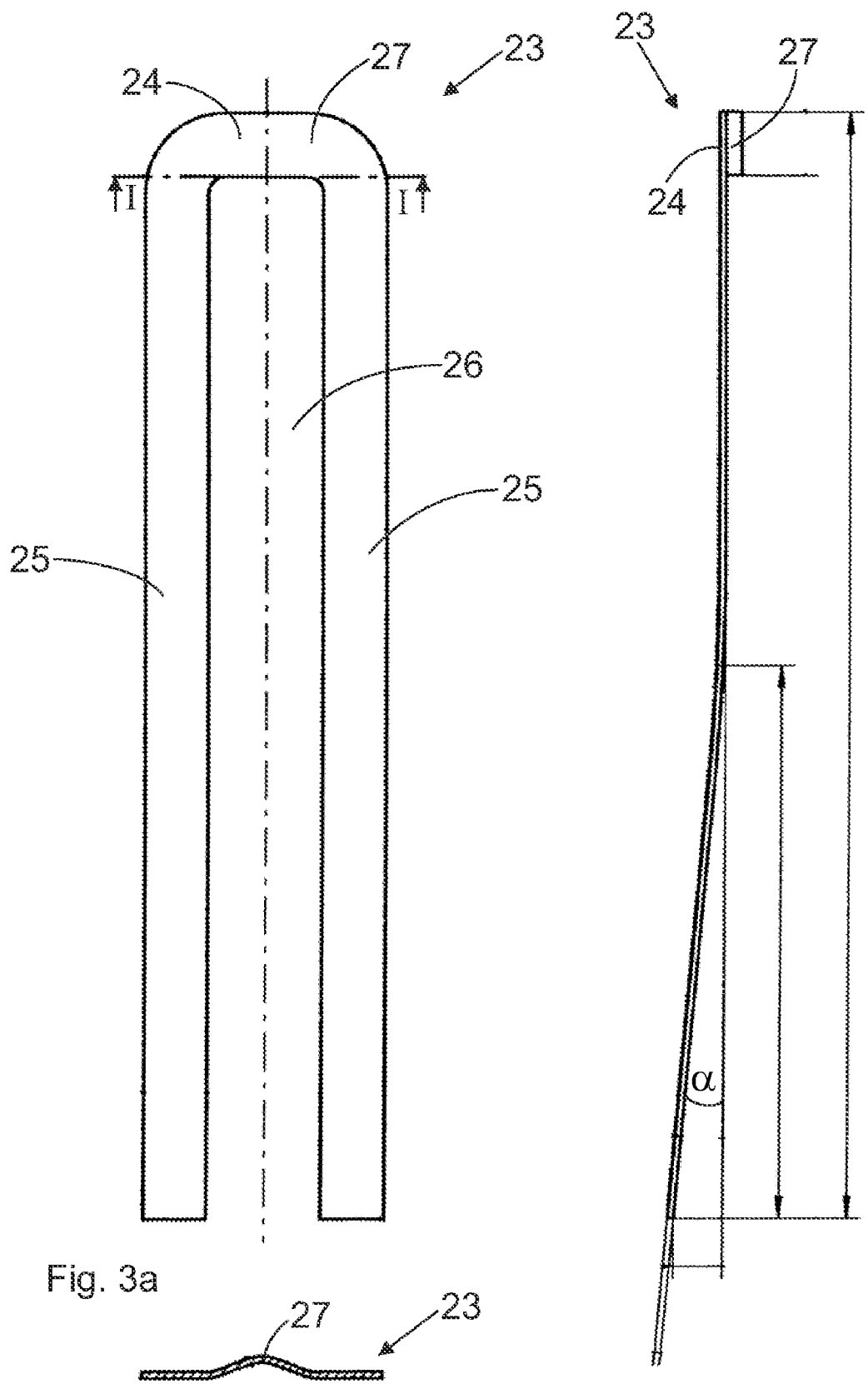
FIG. 3*a* shows a front view of a strap-like support element.
FIG. 3*b* shows a side view of the supporting element from FIG. 3*a*.
FIG. 3*c* shows cross section I-I through the supporting element from FIG. 3*a*.

FIG. 3a shows a curved supporting element 23 which at the same time serves as a coupling section. The curved supporting element 23 is designed to be closed on its cranial end 24. However the supporting element 23 has two open caudal ends 25 which at the same time serve to connect the supporting element 23 to a corset supporting element 41 (not shown). There is a recess 26 which is wide enough for the spine between these two rod-shaped caudal ends 25 of the supporting element 23.

FIG. 3b shows a side view of the curved supporting element 23. This shows clearly that the supporting element 23 is bent at an angle (see angle ∀) approximately at the center, so that the supporting element 23 should follow a healthy curve of the thoracic spine. In addition, this view shows a curve 27 on the cranial end 24 of the supporting element 23. This curve 27 also serves to prevent contact between the supporting element 23 and the thoracic spine.

FIG. 3c shows the cross section I from FIG. 3a. Again in this diagram, the curve 27 for the spine on the cranial end 24 of the supporting element 23 can be seen clearly. In addition, it is apparent that the supporting element 23 is designed to be extremely flat to ensure a high wearing comfort for the thoracic spinal orthotic device. Consequently, the abovementioned reinforcing elements can be attached to the flat caudal ends 25 with no problem.

Figure 4A:
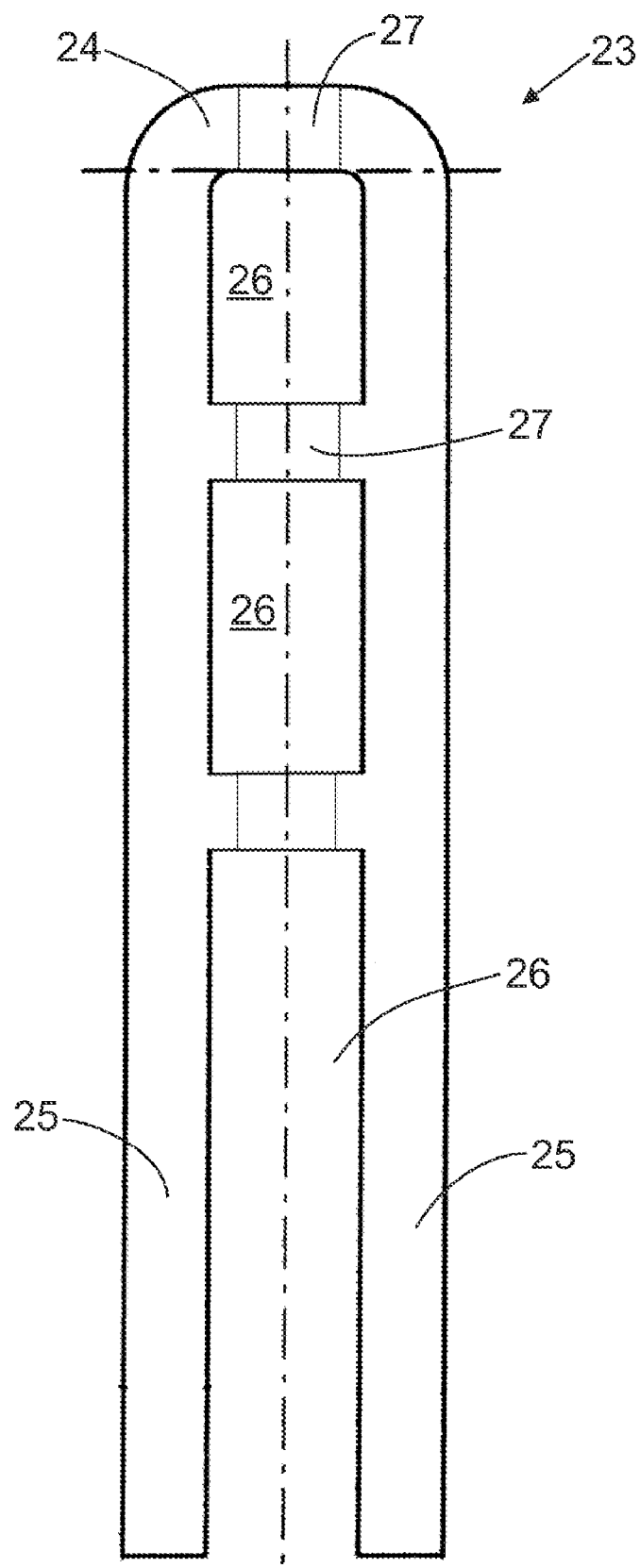
FIG. 4*a* shows a front view of another supporting element.
Figure 4B:
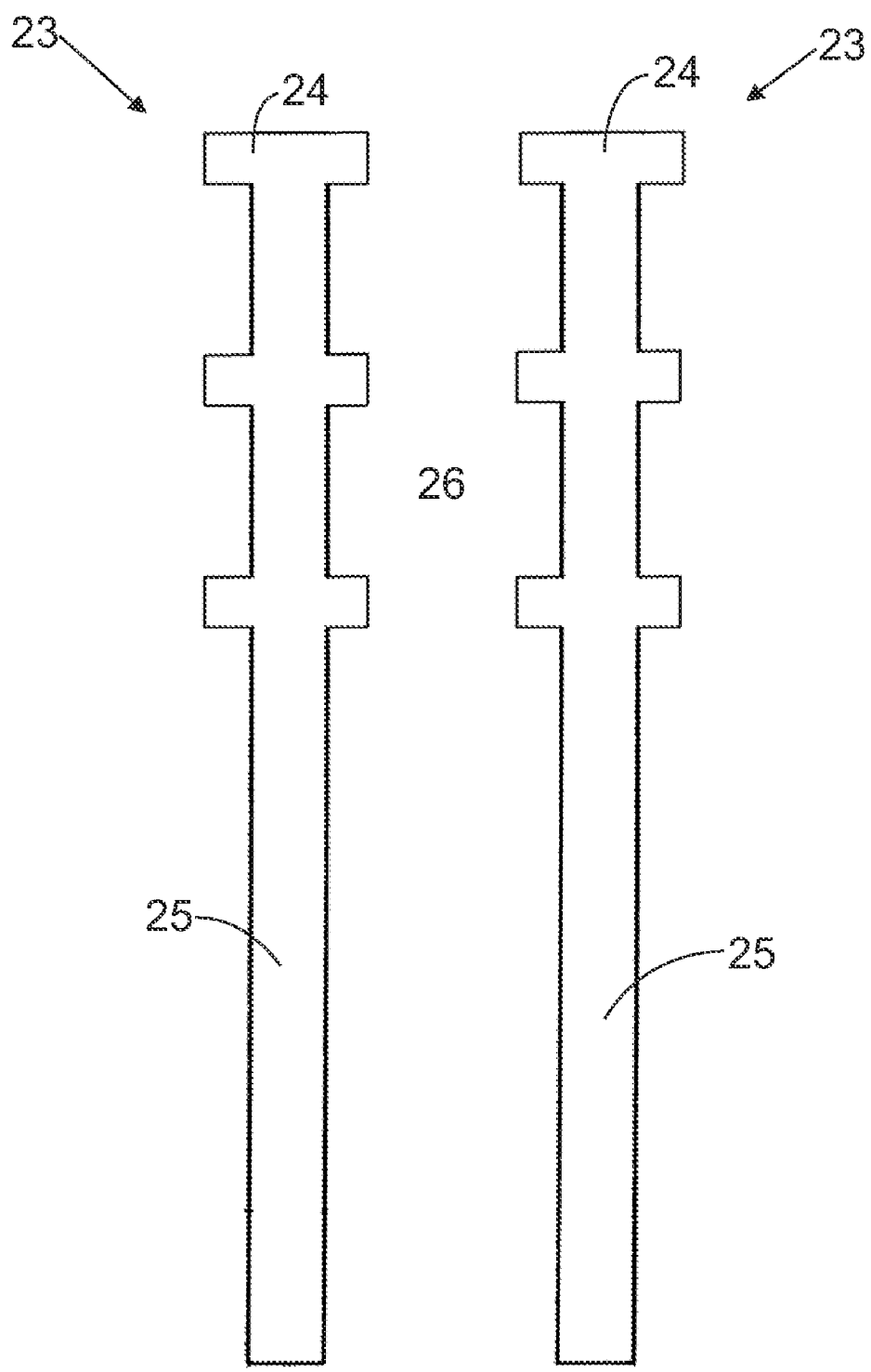
FIG. 4*b* shows a front view of another supporting element.

FIGS. 4a and 4b show other supporting elements 23 in different embodiments. FIG. 4a also shows a strap-shaped supporting element 23, where additional transverse struts connect the caudal ends 25 of the supporting element 23, which may also have curves 27. Thus an increased stability of the supporting element 23 is achieved. Furthermore, this also facilitates the fastening of the supporting element 23 to the posterior part 11 and/or the pockets 21. The bottom transverse struts may serve as a stop element for the counter-coupling element 48.

FIG. 4b shows two identical rod-shaped supporting elements 23 in a view from above. This supporting element 23 also has transverse struts for the longitudinal profile of the supporting element 23. Such a supporting element 23 may be arranged on the right and left sides of the spine. Here again, the caudal end 25 of the supporting element 23 provides the connection to the corset supporting element 41. Two corset supporting elements 41 with suitable designs are expediently also used as counter-coupling elements 48 when two rod-shaped supporting elements 23 are used, as shown in FIG. 4b. The transverse struts mentioned above may serve as stops here so that the rod-shaped supporting elements 23 can cooperate with the corset supporting element 41 only to a predetermined depth.

Figures 5A, 5B:
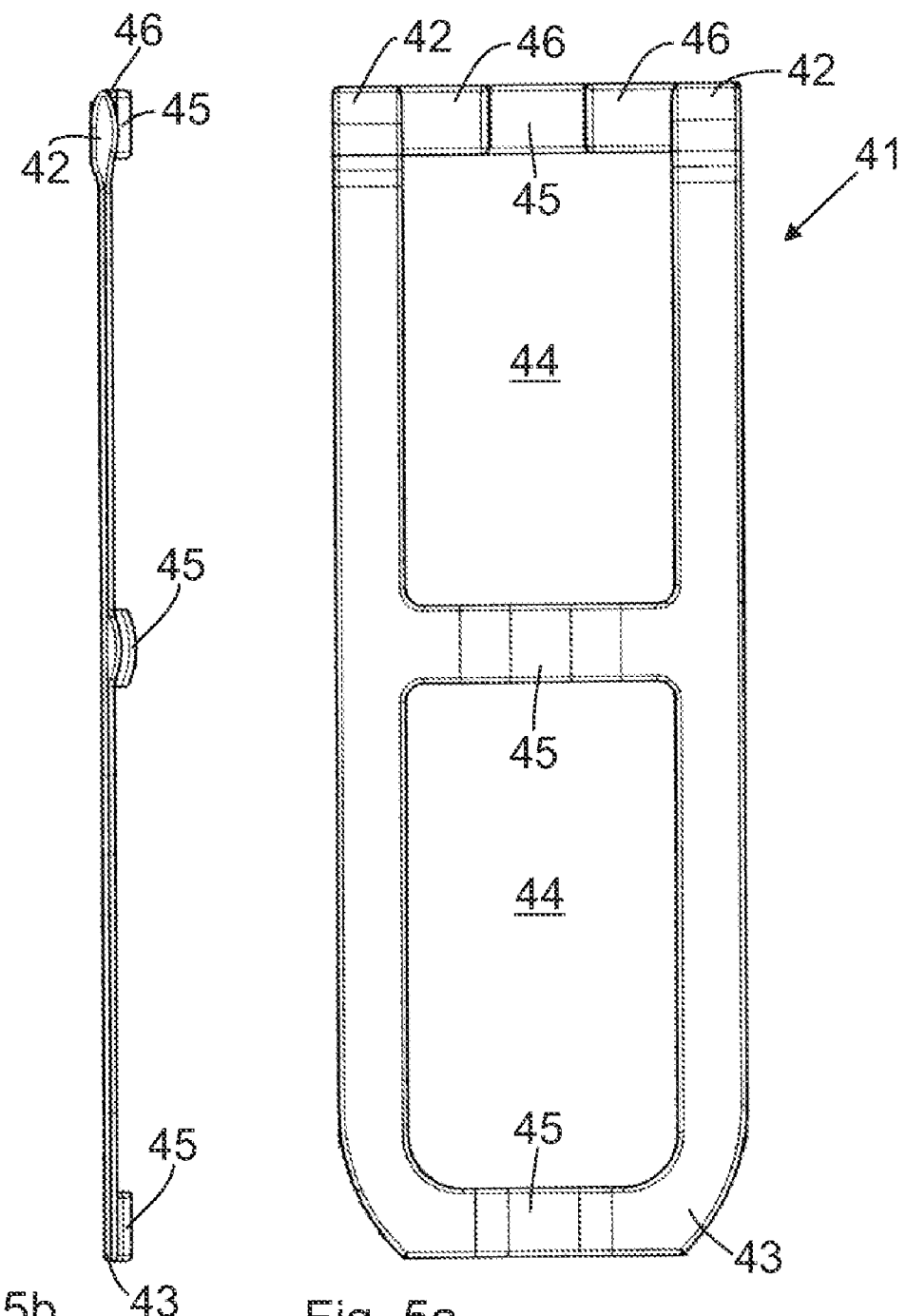
FIG. 5*a* shows a front view of a corset supporting element.
FIG. 5*b* shows a side view of the corset supporting element from FIG. 5*a*.

FIG. 5a shows a frame-like corset supporting element 41. This frame part has two longitudinal rods which are connected to one another with a total of three transverse struts. A receptacle area 46 is provided on the cranial end 42 of the corset supporting element 41 to be able to accommodate a corresponding supporting element 23 in a form-fitting connection. The receptacle area 46 consists of a passage or a bore through which the rod-shaped flat ends 25 of the supporting element 23 can be passed. In this way, the coupling element 28 which consists of the supporting element 23 with the counter-coupling element 48 which is embodied by the corset element 41 can be telescoped together. The supporting elements 23 and 41 which are thus joined together provide adequate stability for the spine in the sagittal plane.

Figure 5C:
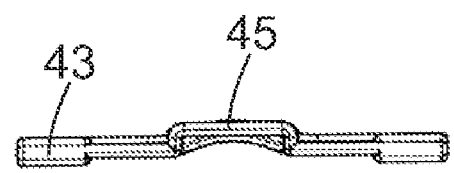
FIG. 5*c* shows a rear view of the corset supporting element from FIG. 5*a*.

FIG. 5b shows a side view of the frame-like corset supporting element 41 from FIG. 5a. It is clear here that the transverse struts are also guided in a curve 45 around the spine. Recesses 44 are also provided in the frame-like corset supporting element 41 to provide adequate room for the spine. FIG. 5c shows a rear view of the corset supporting element 41 from FIG. 5a.

Figure 6:
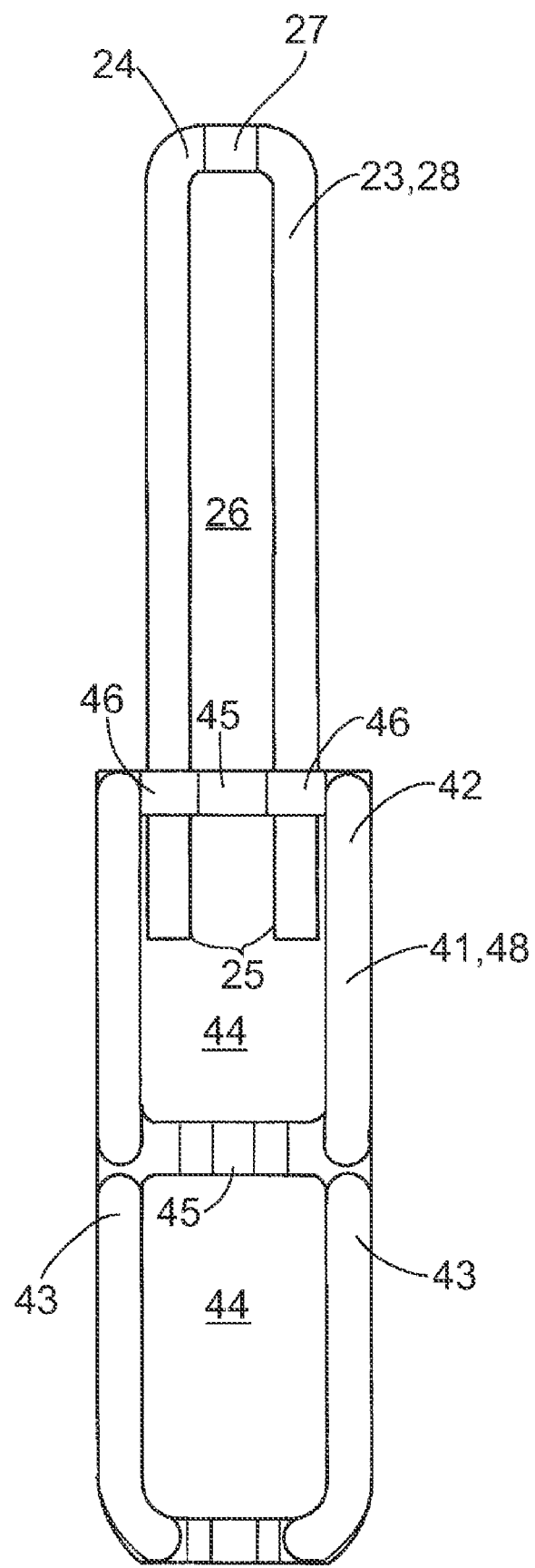
FIG. 6 shows a front view of an assembled supporting element with a corset supporting element and/or a coupling member with a counter-coupling member.

FIG. 6 shows the assembled coupling element 28 with the counter-coupling element 48. The coupling element 28 is inserted with the caudal ends 25 into passages of the receptacle areas 46 in the counter-coupling element 48. Thus the supporting element 23 and/or the coupling element 28 is joined to the corset supporting element 41 and/or the counter-coupling element 48 in a form-fitting connection. In this way, the required stability of the thoracic spinal orthotic device in the sagittal plane is achieved. In addition, other receptacle areas 46 may be provided in the counter-coupling element 48 to increase the stability of the two supporting elements 23 and 24 that are joined together. In addition, an adapter part 30 may also be used. In the present example from FIG. 6, the frame-like corset supporting element 41 has additional reinforcing elements.

Figure 7:
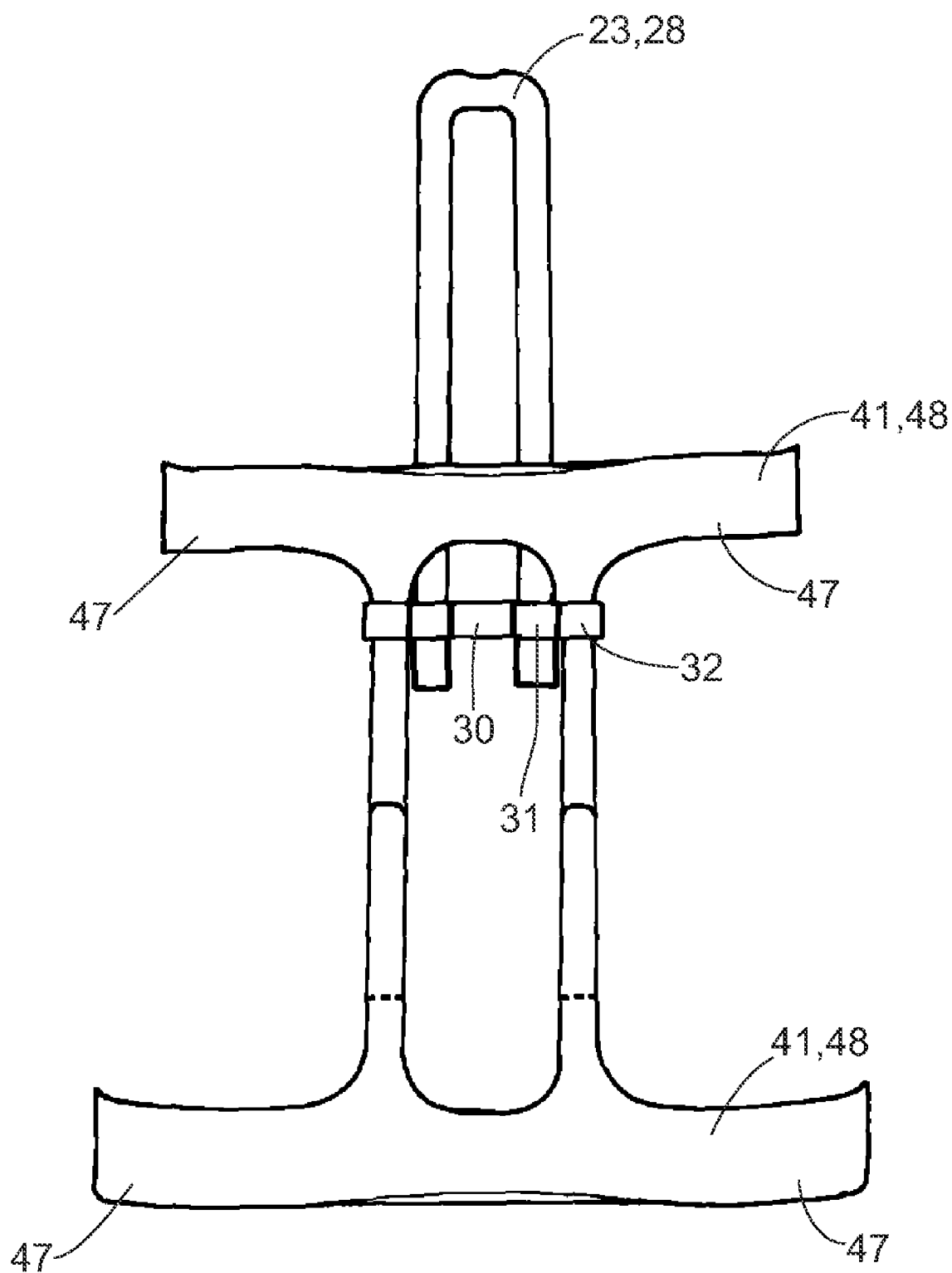
FIG. 7 shows a three-dimensional view of an assembled supporting element with a corset supporting element, two curved supporting clasps being arranged thereon.

FIG. 7 shows another example of a supporting element 23 and a corset supporting element 41. In addition, an adapter part 30 is used here to improve the stability of the connection between the coupling element 28 and the counter-coupling element 48. This adapter part 30 is held so that it is longitudinally displaceable on the rods of the frame-like corset supporting element 41. In addition, the adapter part 30 has two different receptacle areas 31 and 32. The receptacle area 31 provides a form-fitting receptacle for the supporting element 23 whereas the receptacle area 32 provides a form-fitting receptacle for the corset supporting element 41. Furthermore, two curved supporting clasps 47 are arranged on the frame-like corset supporting element 41. The corset supporting element 41 from FIG. 7 in the present case is itself designed in two parts, with the two parts being connected by the rod-shaped elements of the corset supporting element 41. Due to the two-part design of the corset supporting element 41, an adjustment in size is possible, so that this orthotic device, in particular the thoracolumbar orthotic device, is designed to be optimally adaptable to the patient's body. Due to the two-part corset supporting element 41 with the curved supporting clasps 47, the spine is supported not only in the sagittal plane but also in the frontal plane. As this shows clearly, the curved supporting clasps 47 are arranged orthogonally to the two longitudinal rods of the corset supporting element 41. The curved supporting clasp 47 may be connected to the respective longitudinal rods of the corset supporting element 41 so they are made of the same material in one piece. The open ends of the longitudinal rods of the corset supporting element 41 can be joined together in a form-fitting manner by means of catch means and counter-catch means. It is also conceivable to join the aforementioned ends together via hook-and-loop fasteners (also called VELCRO-type closures) or push-buttons or the like.

Figure 8:
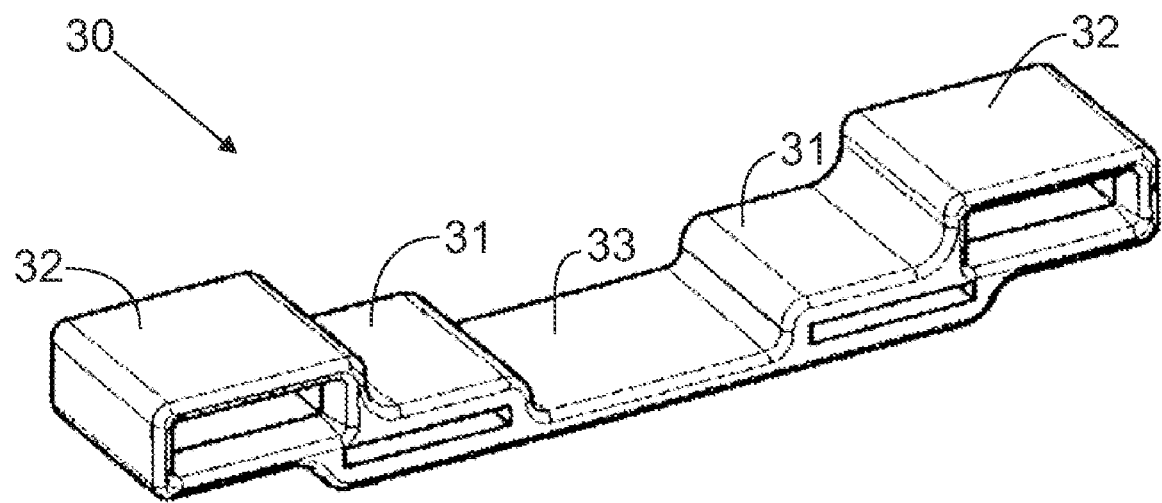
FIG. 8 shows a three-dimensional view of an adapter part.

FIG. 8 shows a three-dimensional view of the adapter element 30. The receptacle areas 32 for the rod-shaped ends of the corset supporting element 41 are arranged in the right and left sides. They consist essentially of a passage designed to be rectangular. The receptacle areas 31 for the open rod-shaped ends of the supporting element 23 are connected to the receptacle areas 32. These receptacle areas 31 also have rectangular passages. In order for the adapter part 30 not to press against the patient's spine, a central recess 33 is also provided, connected to the receptacle areas 31 on the right and left sides toward the inside. FIG. 7 illustrates the use of the adapter part 30. As already mentioned, this adapter part 30 is attached to the rod-shaped ends of the corset supporting element 41 so that it is adjustable in height. The caudal ends 25 of the supporting element 23 may protrude variably into the receptacle area 31 of the adapter part 30. The stability of the assembled supporting elements 23 and 24 can be varied merely through the adjustability in height of the adapter part 30. The adapter part 30 may itself be made of plastic or a metal part, in particular a light metal alloy.

Figure 9:
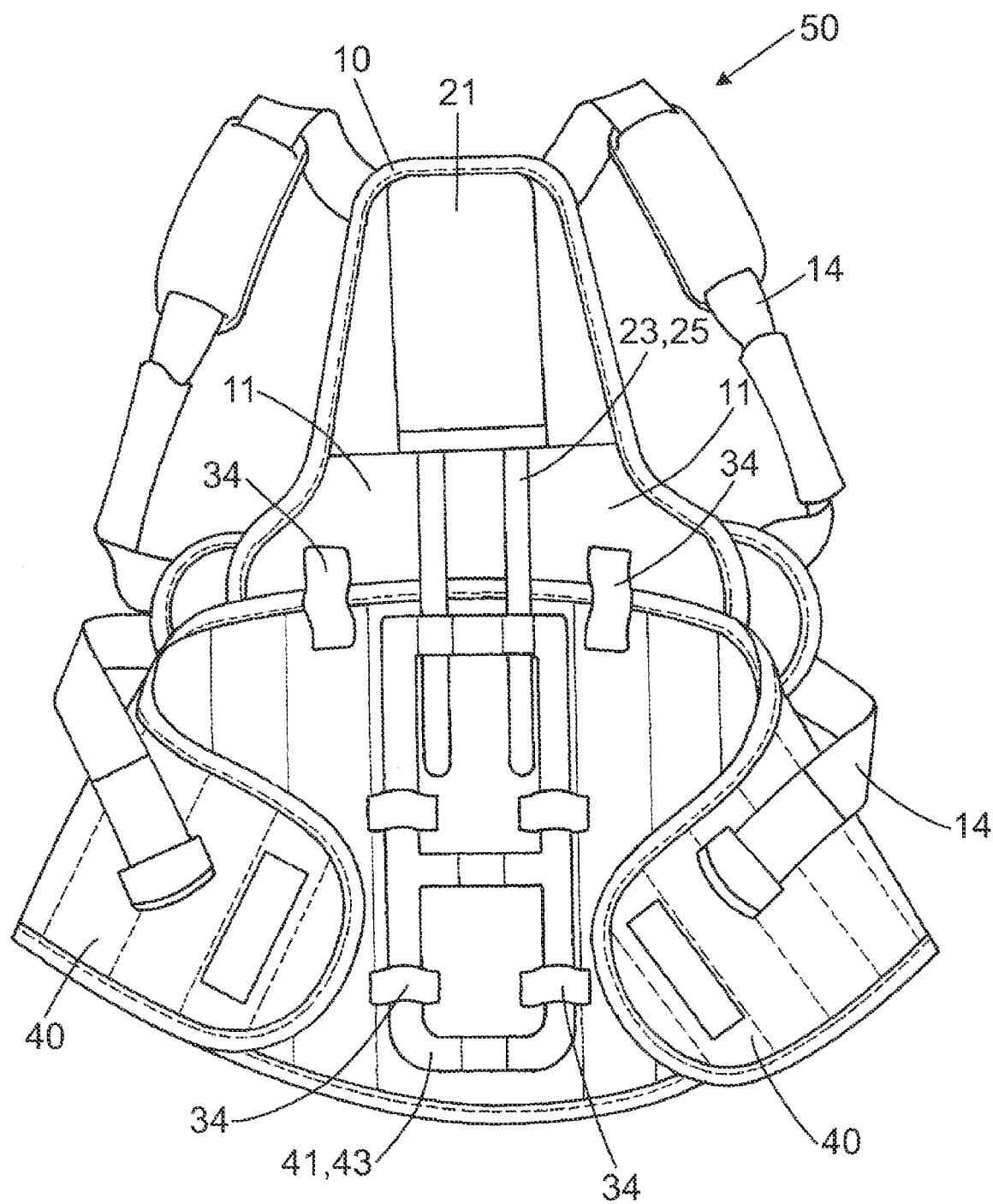
FIG. 9 shows a three-dimensional view of an inventive vertebral orthesis without the curved supporting clasp.

FIG. 9 shows a spinal orthotic device 50. This spinal orthotic device 50 is obtained by joining the thoracic spinal orthotic device 10 with the lumbar spinal corset 40. First, the supporting element 23, and secondly, the corset supporting element 41, which together form a coupling element 28 and a counter-coupling element 48, serve to couple the thoracic spinal orthotic device 10 and the lumbar spinal corset 40. The supporting element 23 is arranged in a stationary position in the posterior part 11 in the pocket 21. The corset supporting element 41 can be secured by a comparable pocket on the inside of the lumbar spinal corset. It is also conceivable, as in the present case, to attach the frame-like corset supporting element 41 by means of VELCRO-type fasteners 34. It should be pointed out here that both the supporting element 23 and the corset supporting element 41 can be secured by means of other connecting means such as pushbuttons, catch means and counter-catch means, for example. The spinal orthotic device 50 shown in FIG. 9 supports the spine exclusively in the sagittal plane.

The thoracic spinal orthotic device 10 shown in FIG. 9 is connected to the lumbar spinal corset 40 by additional connecting elements, e.g., VELCRO-type closures. However, this does not provide any support for the spine. Instead, a corresponding adjustment in the spinal orthotic device to the patient's body size is possible. To this end, the coupling element 28 is also adjustable in relation to the counter-coupling element 48.

Figure 10:
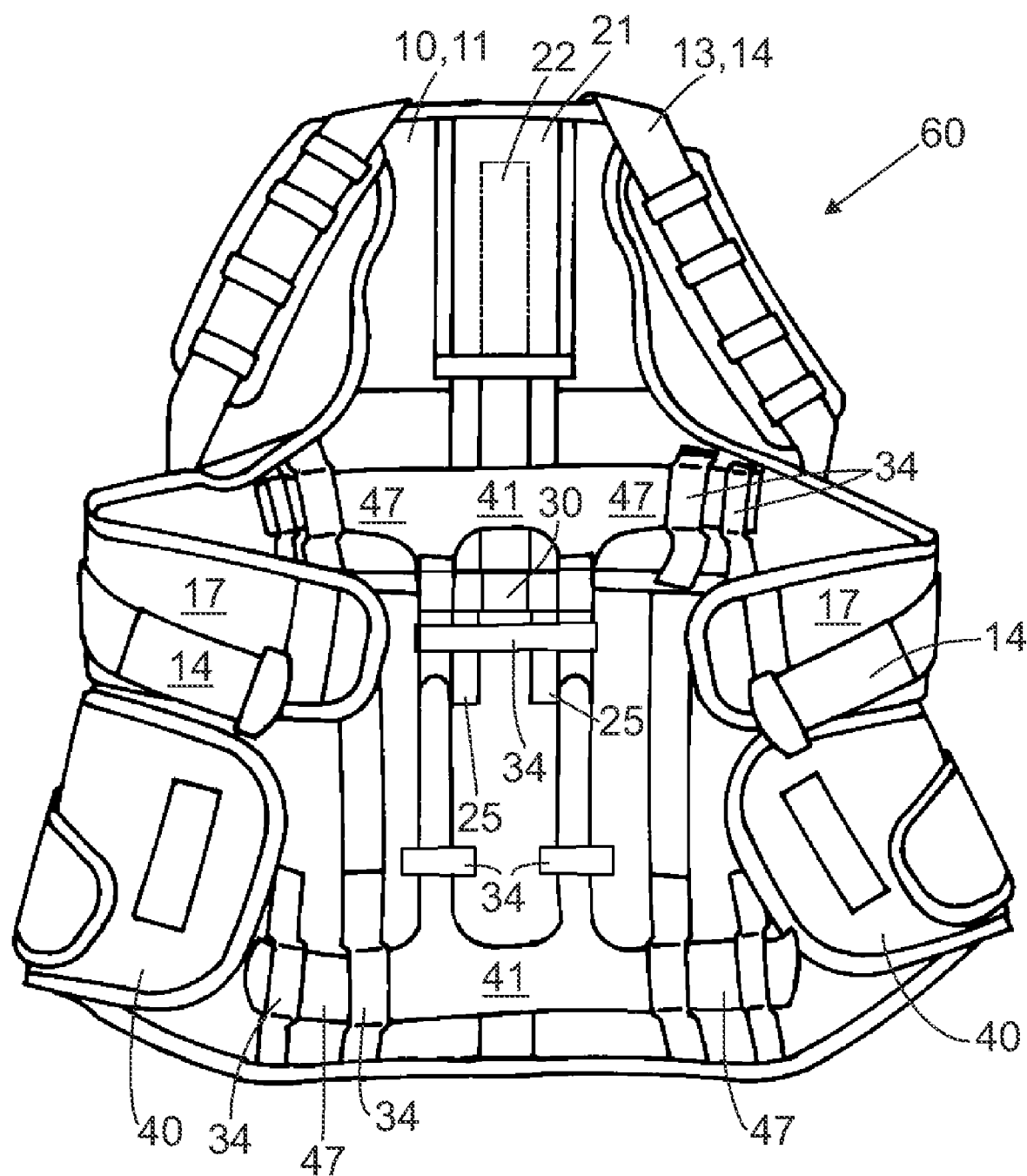
FIG. 10 shows a three-dimensional view of a thoracolumbar orthotic device.

FIG. 10 shows a thoracolumbar orthotic device 60. With this orthotic device 60, the combination of the supporting element 23 is used with the corset supporting element 41 from FIG. 7. Thus the thoracolumbar orthotic device 60, which consists of the thoracic spinal orthotic device 10, a shoulder strap system 17 with the lumbar spinal corset 40, supports the patient's spine in the sagittal and frontal planes. The thoracic spinal orthotic 10 is joined via the coupling element 28 and the counter-coupling element 48. In addition, other connecting means are also provided in the form of VELCRO-type closures, pushbuttons or the like. The counter-coupling element 48 is held on the lumbar spinal corset 40 in a form-fitting manner by means of VELCRO-type closures 34. The corset supporting element 41 in the present case has two curved supporting clasps 47 which are arranged orthogonally to the rods of the corset supporting element 41.

Figure 11:
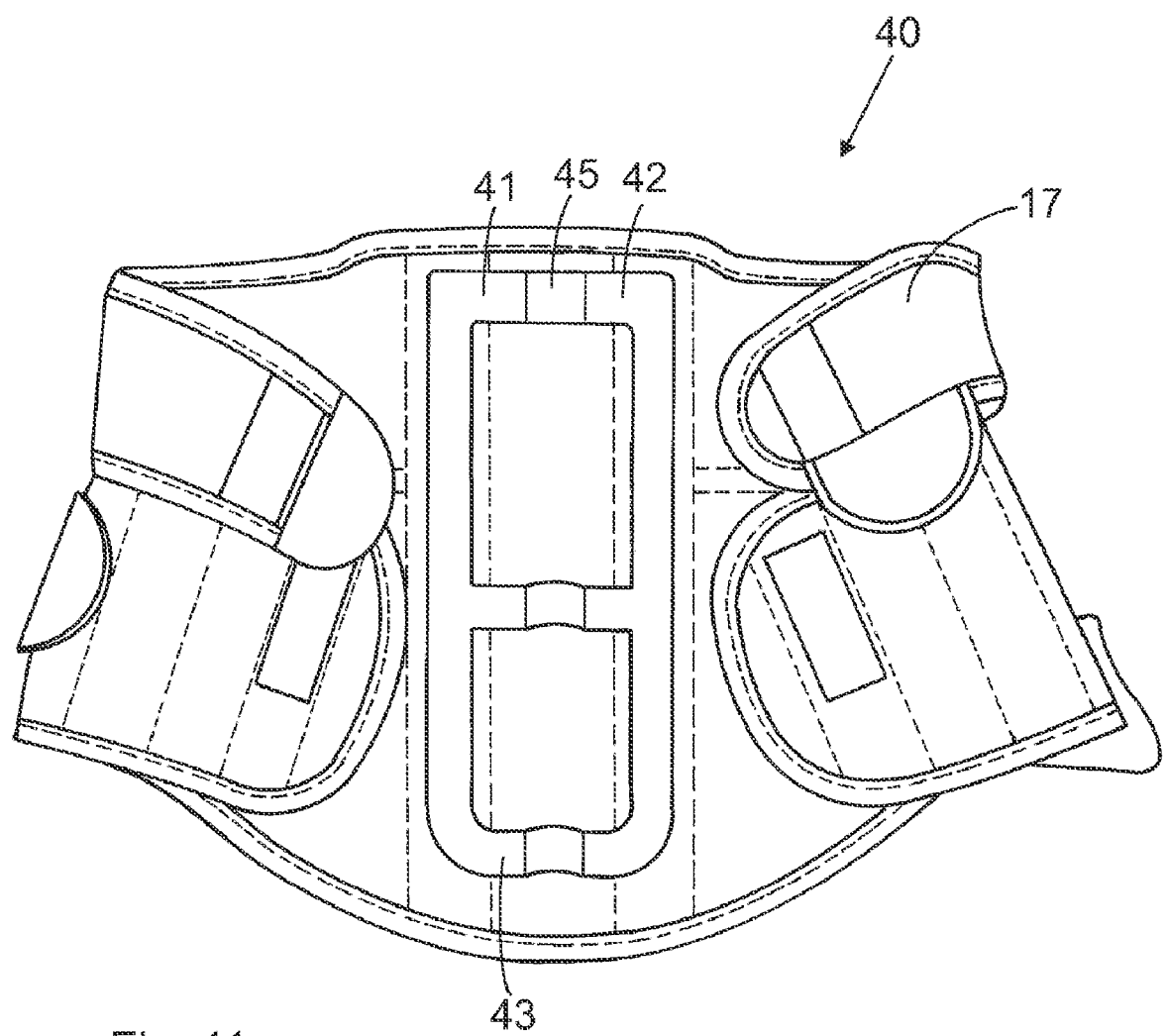
FIG. 11 shows a three-dimensional view of a lumbar vertebral corset and FIG. 12*a* shows a front view of a belt holder and FIG. 12*b* shows section II-II through the belt holder from FIG. 12*a*.

FIG. 11 shows a complete usable lumbar spinal corset 40. This may be connected cranially to a shoulder strap system 17 and/or an upper abdominal corset 17. This shoulder strap system 17 can in turn be connected cranially to the thoracic spinal orthotic device 10. The lumbar spinal corset 40 can also be used alone if the patient has problems only in the area of the lumbar spine. To this end, the corset supporting element 41 may be secured on the inside of the lumbar spinal corset 40, in particular in a form-fitting manner. Pockets 21 or VELCRO-type closures 34 may be used for the arrangement of the corset supporting element 41. The lumbar spinal corset 40 may be supplemented cranially by the thoracic orthotic device 10 to form a thoracic/lumbar orthotic device.

Figure 12B:
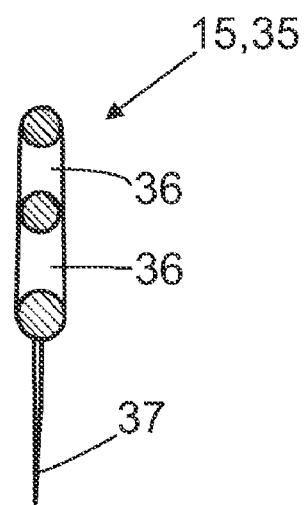
Figure 12A:
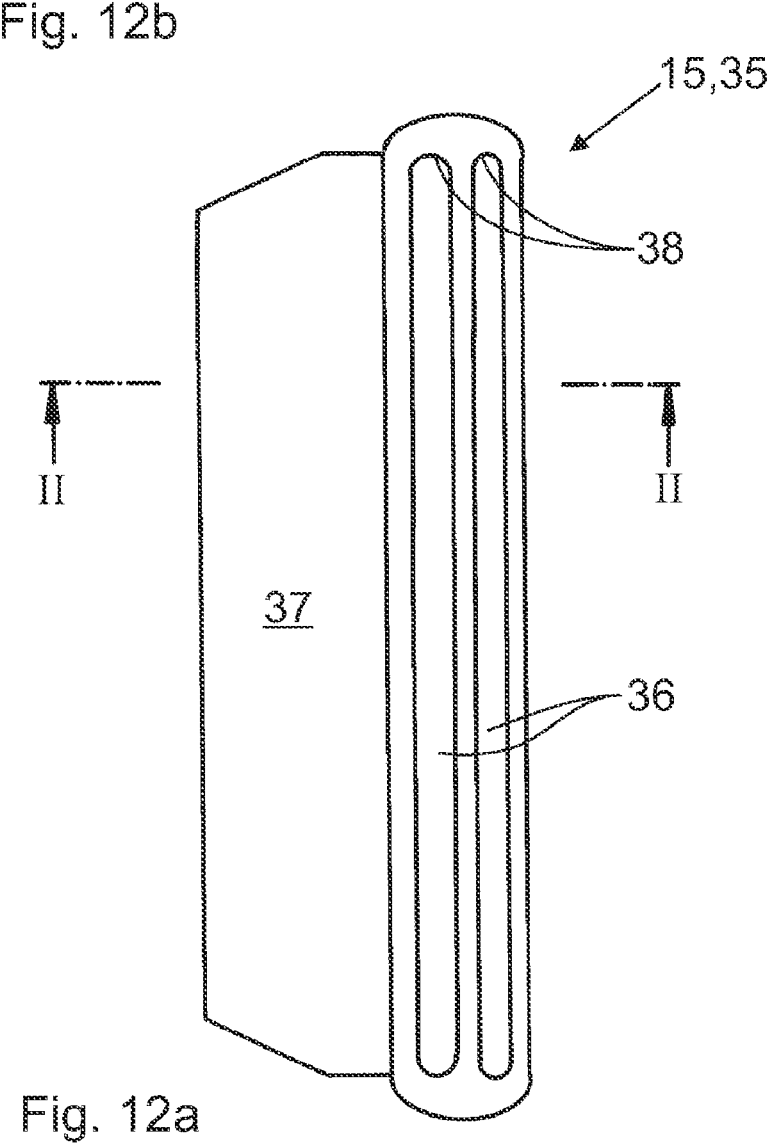

FIGS. 12a and 12b show a belt holder 15 with a guide strap 35. This guide strap 35 has at least two pull-through straps 36 that are separate from one another and are designed to be wide but narrow to be able to accommodate the inelastic belt 14 and/or the elastic belt 16. As FIG. 12a shows, the corners 38 of the respective pull-through strap 36 are rounded. In addition, these corners 38 may also be designed to be reinforced to avoid tears or cuts in the belts and/or belts to chafed areas. In addition, a sewed-on tab 37 is provided on the guide strap 35, this tab having approximately the same width as the inelastic belt 14. This sewed-on tab 37 serves to allow additional sewing of the elastic belt 16 to the guide strap 35 to prevent the elastic belt 16 from bunching up on the belt holder 15.

FIG. 12b shows section II from FIG. 2a, which clearly shows the separation of the two pull-through straps 36. The wedge-shaped course of the sewed-on tab 37, which is designed to decrease in size away from the guide strap 35 can also be seen here.

FIGS. 14, 17, 21, 22, 24, 26 and 28 show seven different orthotic devices that can be configured out of this modular system. The other figures show individual elements of the modular system that do not yet form a wearable orthotic device.

Figure 13:
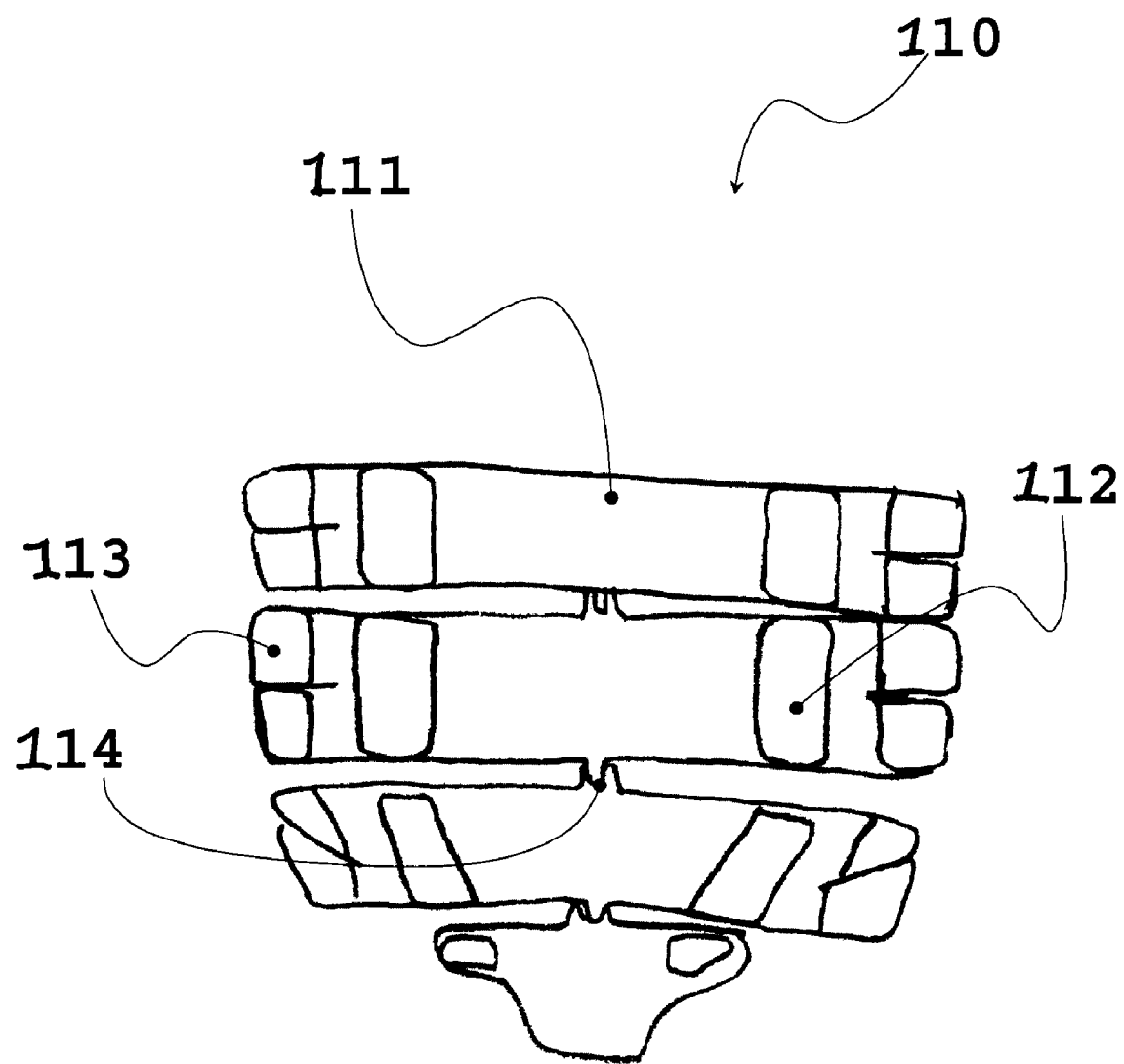
FIG. 13 shows a sectional truss pad.
Figure 14:
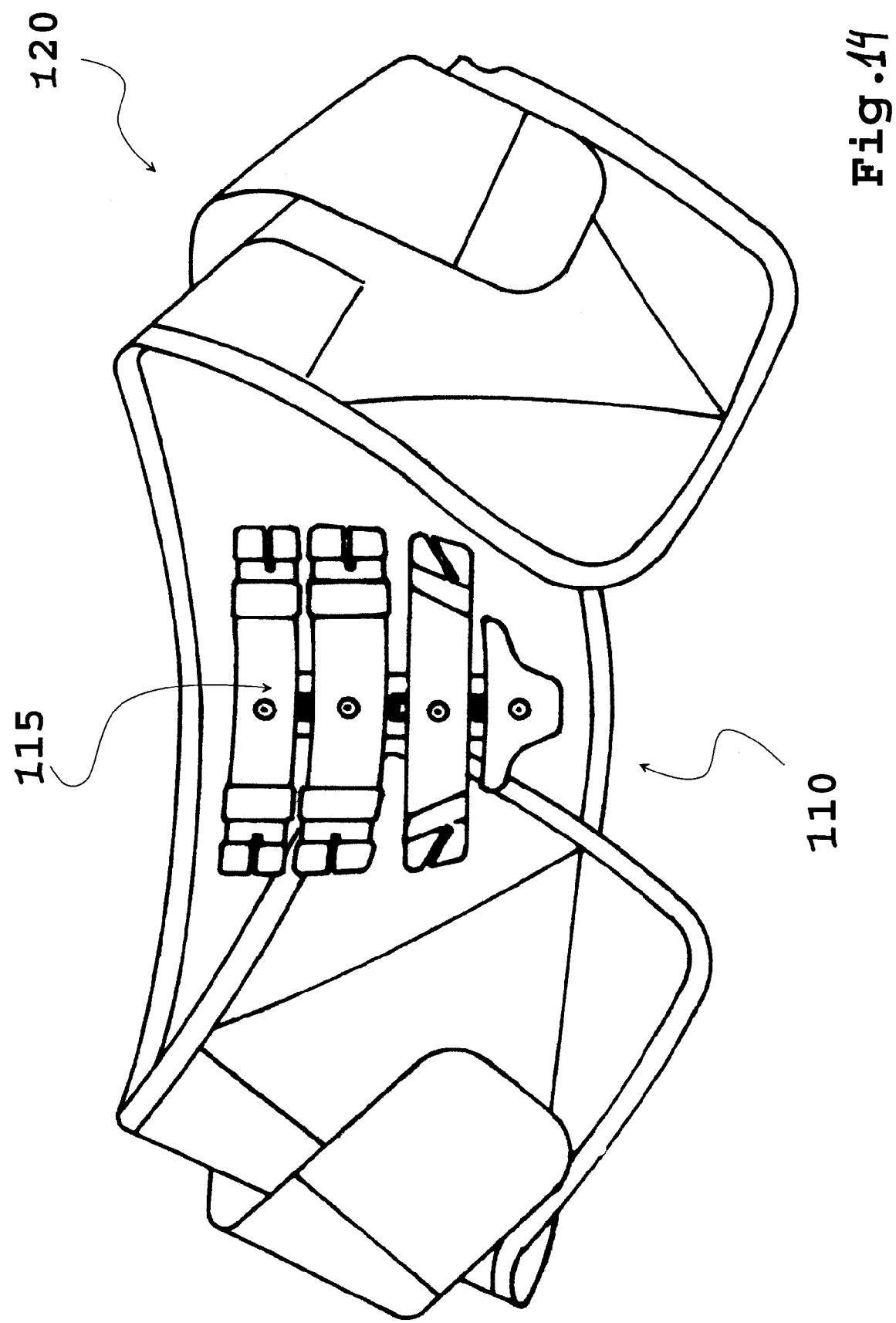
FIG. 14 shows stabilizing orthotic device.
Figure 16:
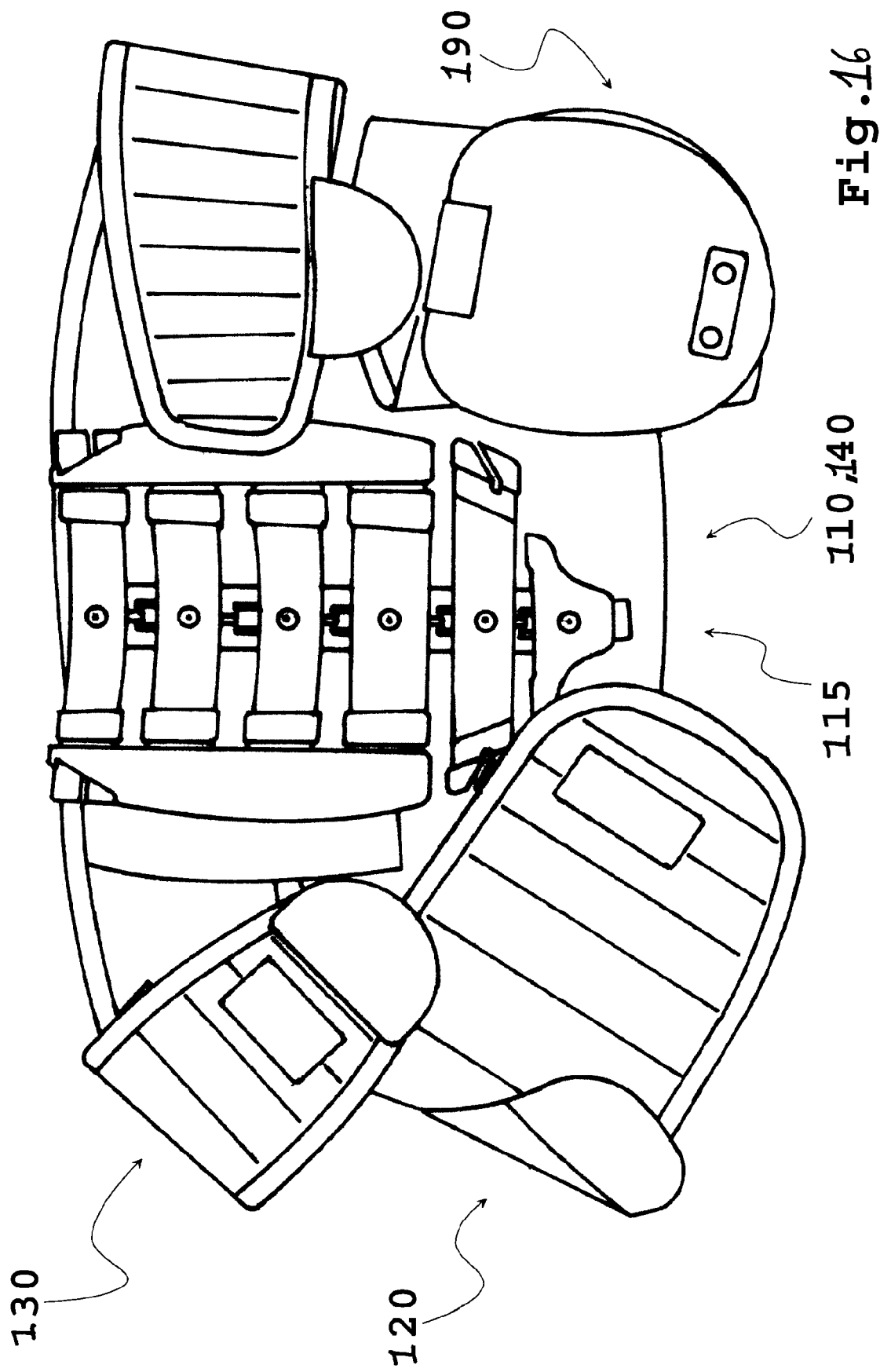
FIG. 16 shows a fixation element.
Figure 19:
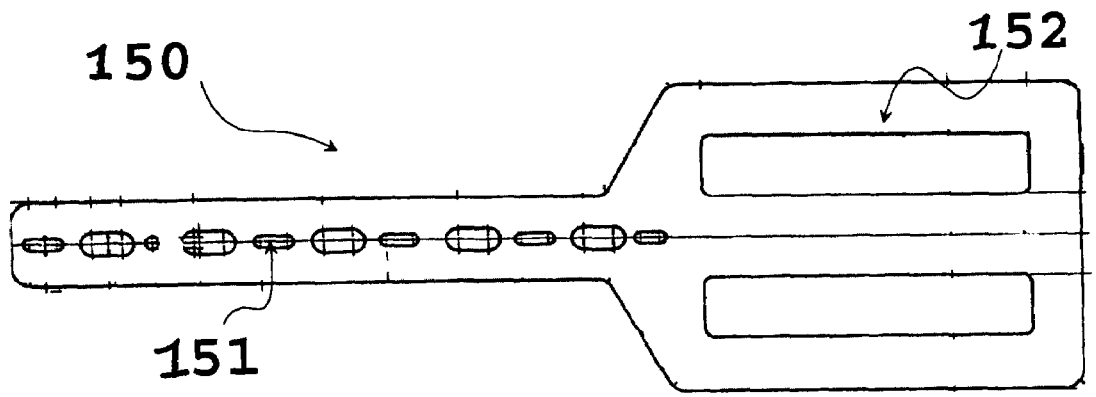
FIG. 19 shows a connecting element.

An essential basic element of the second basic modular system is the basic truss pad in the form of a sectional truss pad 110, as shown in FIG. 13. This consists of four sections 111 joined together with an articulation, each section being assigned to one vertebra. The bottom section is assigned to the first sacral vertebra (S1), and the three other sections are assigned to the third to fifth lumbar vertebrae (L3-L5). The sections 111 are designed in the manner of a bridge, bridging "their" vertebrae transversely and each lying with contact surfaces 112 on both sides of the vertebra on the back. Laterally the sections 111 assigned to the lumbar vertebrae do not have insertion ends 113 on the back onto which supporting rails 142 of the lumbar extension 140 described later can be placed. The sections 111 of the sectional truss pad 110 can be joined together with an articulation with the help of joints 114, so that the individual sections 111 are movable with respect to one another in all three planes (frontal, sagittal and transverse planes). This mobility is restricted by optional use of a fixation element 115 as shown in FIG. 16 or a connecting element 150 as shown in FIG. 19 posteriorly on the sectional truss pad 110. To this end, the individual sections 111 of the sectional truss pad 110 have pushbuttons on their backside engaging in recesses 151 in the fixation element 115 and/or the connecting element 150. The individual sections 111 of the sectional truss pad 110 are thereby secured immovably with respect to one another in the sagittal plane so that only a certain freedom of movement in the transverse and frontal planes remains in the lower lumbar area.

The sectional truss pad 110 whose sagittal mobility is restricted by the fixation element 115 can be secured dorsally in a lower abdominal corset 120. This yields the stabilizing orthotic device illustrated in FIG. 14, which supports and aligns the lumbar spinal area. To do so, the lower abdominal corset 120 is wrapped around the abdomen accordingly and fastened. This basic orthotic device supports and relieves the lower lumbar area.

Figure 15:
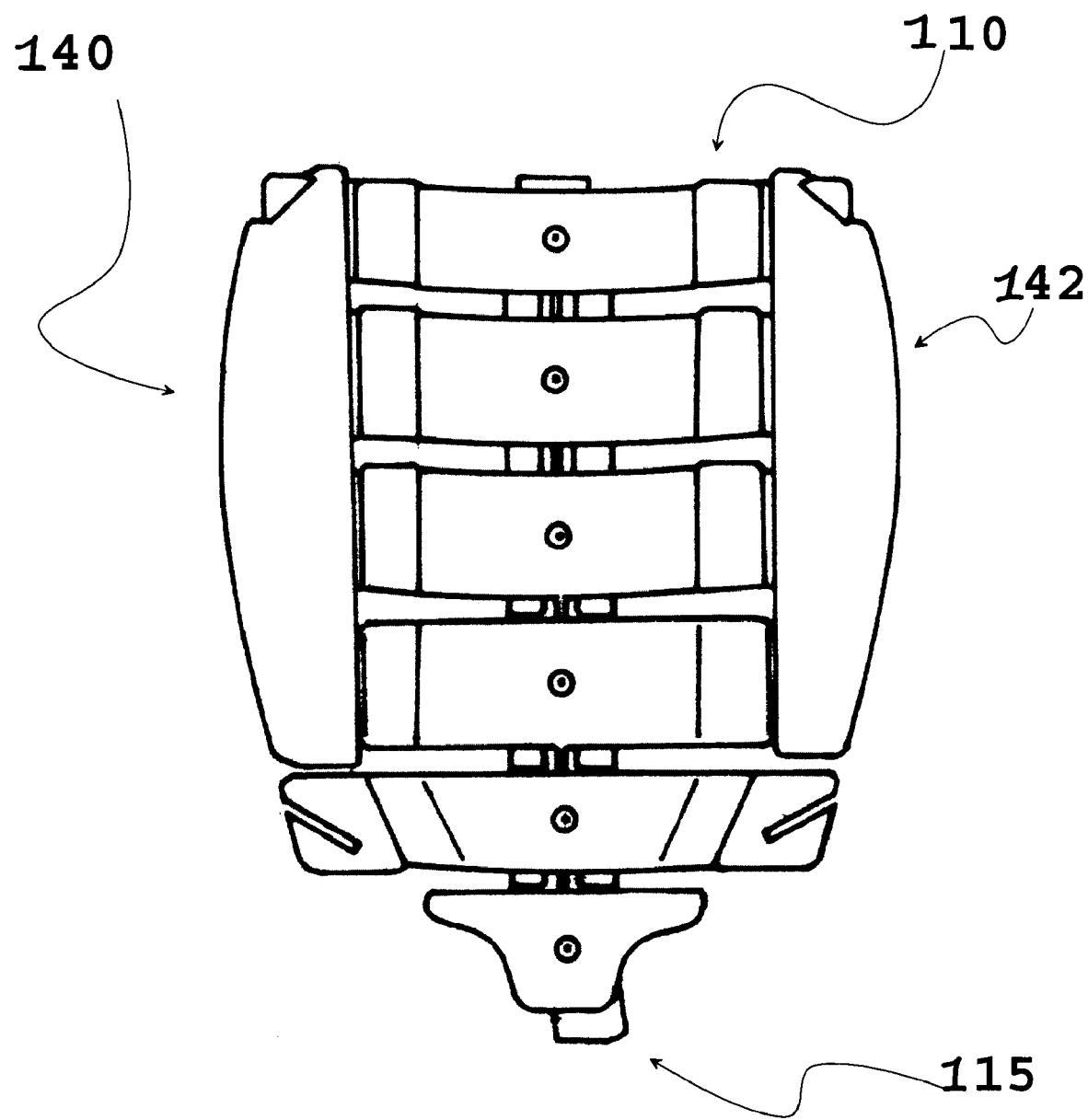
FIG. 15 shows a sectional truss pad with a lumbar extension.

If lordosis of the entire lumbar spine is to be corrected, the sectional truss pad 110 can be extended by adding a lumbar extension 140, as shown in FIG. 15. The lumbar extension 140 comprises two additional sections 141 which are incorporated into the existing sectional truss pad 110, so that the expanded sectional truss pad 110 comprises a total of six sections 111, 141, which cover the entire lumbar area (L1-L5) and the first sacral vertebra (Si). In addition, the lumbar extension 140 comprises two supporting rails 142, which can be attached laterally to the insertion ends 113 of at least the four sections 111, 141 of the expanded sectional truss pad 110, bridging the first four lumbar vertebrae. When the supporting rails 142 are attached, they reinforce the truss pad bandage in all three planes, so that only the sections of the fifth lumbar vertebra and the first sacral vertebra still have free mobility. The patient has only limited mobility within the frontal plane in the area reinforced by the supporting rails 142, while sagittal mobility is completely blocked.

The sectional truss pad 110 expanded by the lumbar extension 140 as illustrated in FIG. 15 can be secured dorsally in the lower abdominal corset 120. Since this does not extend over the entire lumbar spinal area, it is supplemented cranially by an upper abdominal corset 130. The lower and upper abdominal corsets 120, 130 can be secured to one another by VELCRO-type closures. The overlap area between the lower and upper abdominal corsets 120, 130 can be selected freely, so that the corset bandage can be adapted to the patient's body size. To increase the intra-abdominal pressure, an abdominal truss pad 190 can be secured ventrally in the lower abdominal corset 120. The abdominal truss pad 190 is shown in FIG. 13 and will be explained in greater detail below. The orthotic device shown in FIG. 17 consisting of the lower abdominal corset 120, the upper abdominal corset 130, the sectional truss pad 110, the lumbar extension 140, the fixation element 115 and the abdominal truss pad 190 is a lumbar orthotic device that corrects lordosis of the entire lumbar spinal area.

Figure 18:
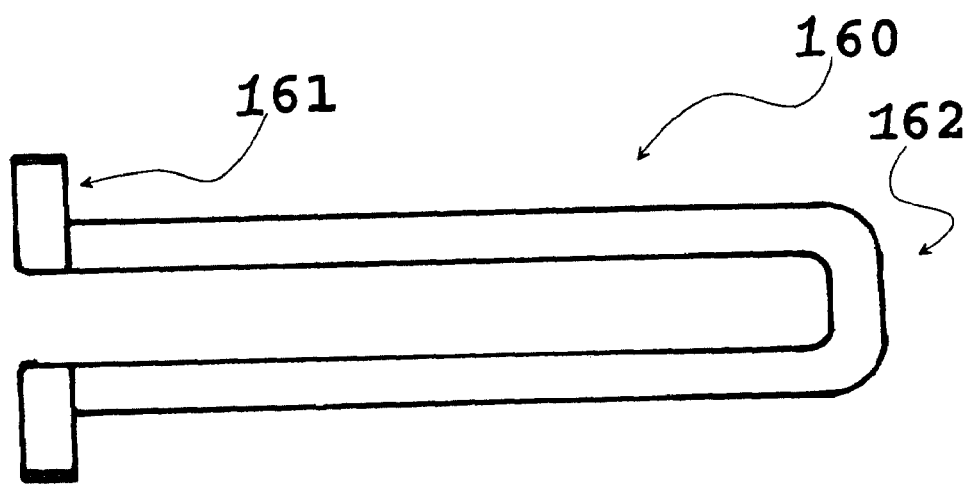
FIG. 18 shows a supporting element.
Figure 21:
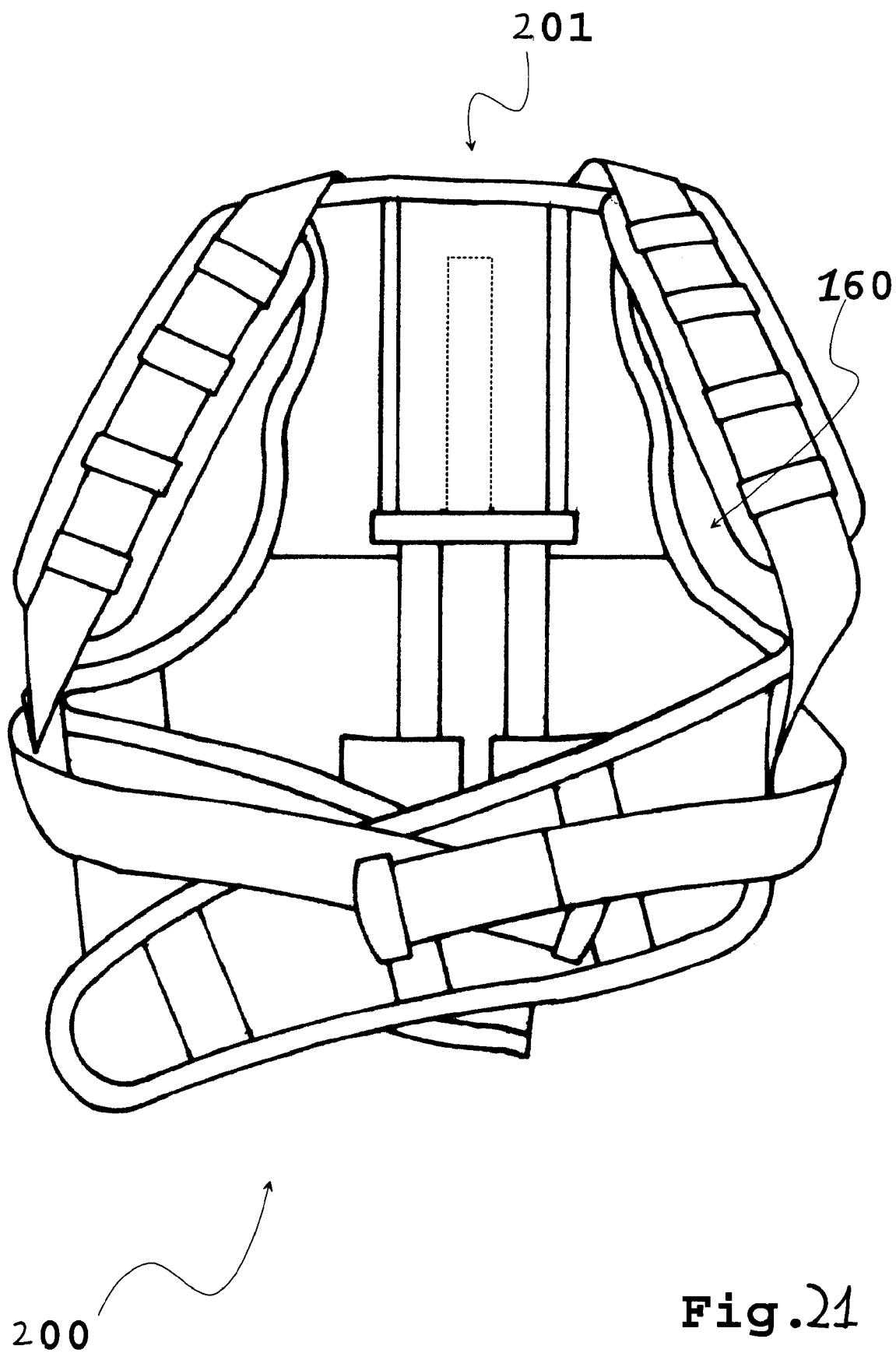
FIG. 21 shows a thoracic orthotic device.

If the spine is also to be supported in the thoracic area, then the sectional truss pad 110 can be expanded with the help of the supporting element 160 shown in FIG. 18. The supporting element 160 is essentially U-shaped and extends with its legs along the spine in the thoracic spinal area. At its caudal end, the supporting element 160 has a securing clamp 161 on each leg with the help of which the supporting element 160 can optionally be secured to the connecting element 150 shown in FIG. 19 or to the bridging frame 170 illustrated in FIG. 23 and described below. At its cranial end 162, the supporting element 160 is inserted into a pocket 201 provided specifically for this purpose and situated posteriorly on a thoracic spinal corset 200 in the form of a backpack. The thoracic spinal corset 200 is shown in FIG. 21 with the supporting element 160 inserted. The supporting element 160 is secured in the pocket 201 of the thoracic spinal corset 200. This orthotic device shown in FIG. 21 can be worn separately as a thoracic orthotic.

Figure 17:
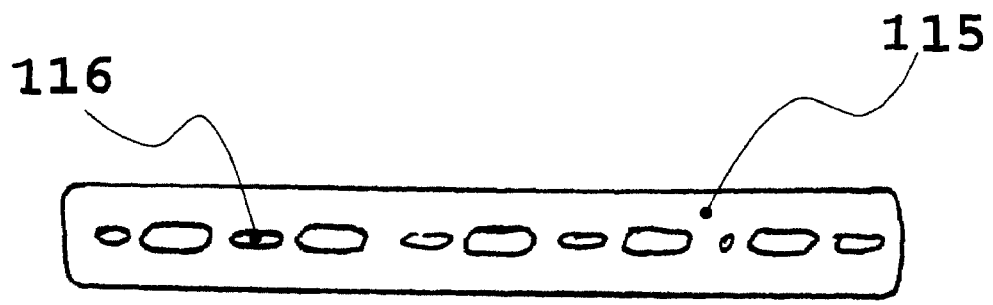
FIG. 17 shows a lumbar orthotic device.
Figure 22:
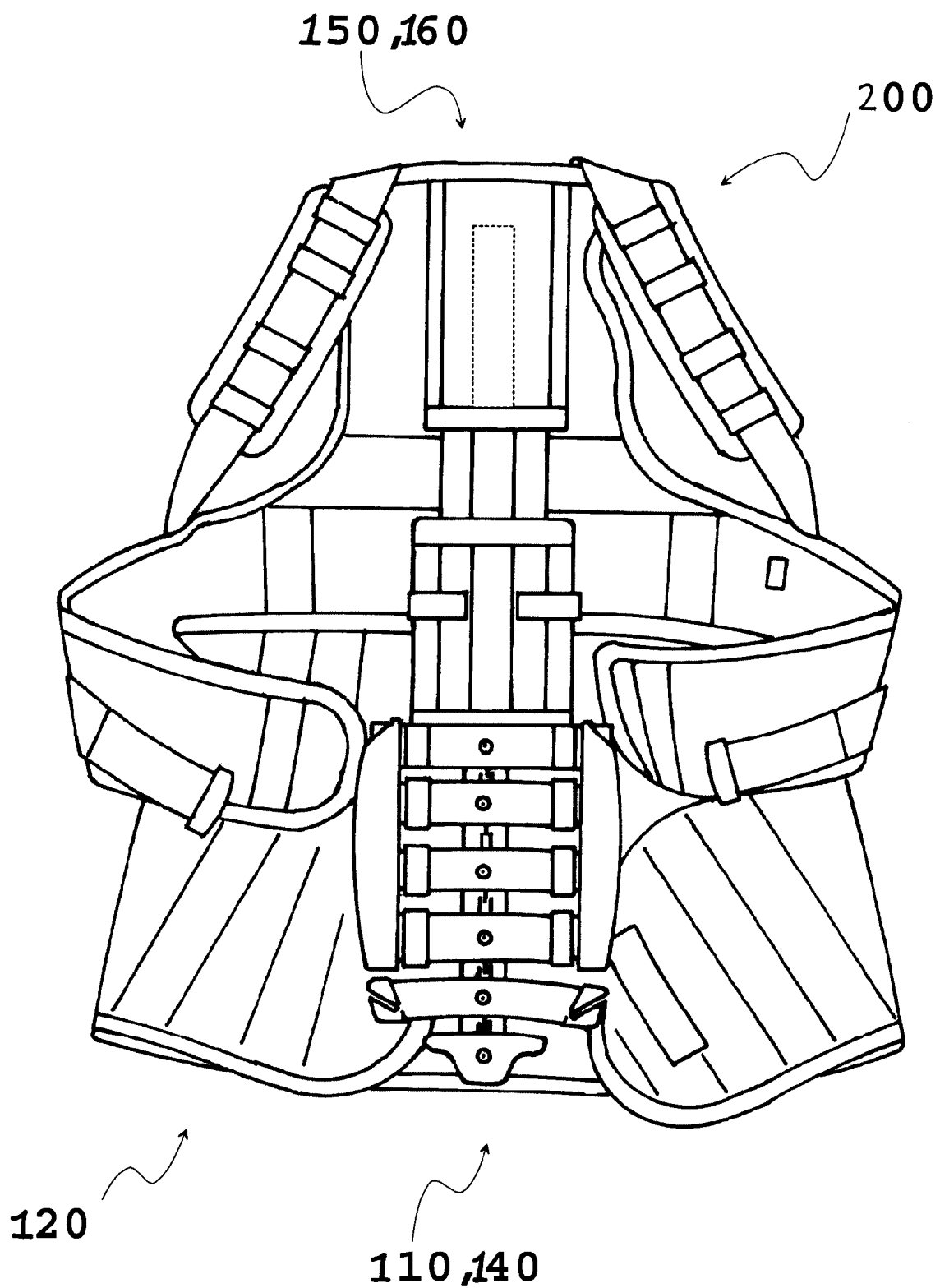
FIG. 22 shows a spinal orthotic device sagittally.

With the help of the supporting element 160 and the thoracic spinal corset 200, the lumbar orthotic device shown in FIG. 17 can be converted to the spinal orthotic device illustrated in FIG. 22 which stabilizes and aligns the entire spine in the sagittal plane. To do so, first the fixation element 115 shown in FIG. 16 is replaced by the connecting element 150 shown in FIG. 19. This has a fork-like receptacle 152 on its cranial end, so that the supporting element 160 with its securing clamps 161 can be secured in this receptacle. This forms the supporting structure illustrated in FIG. 20. This can be adapted to the patient's body size by inserting the securing clamps 121 inside the fork-like receptacle 152 of the connecting element 150 to the required length.

Figure 20:
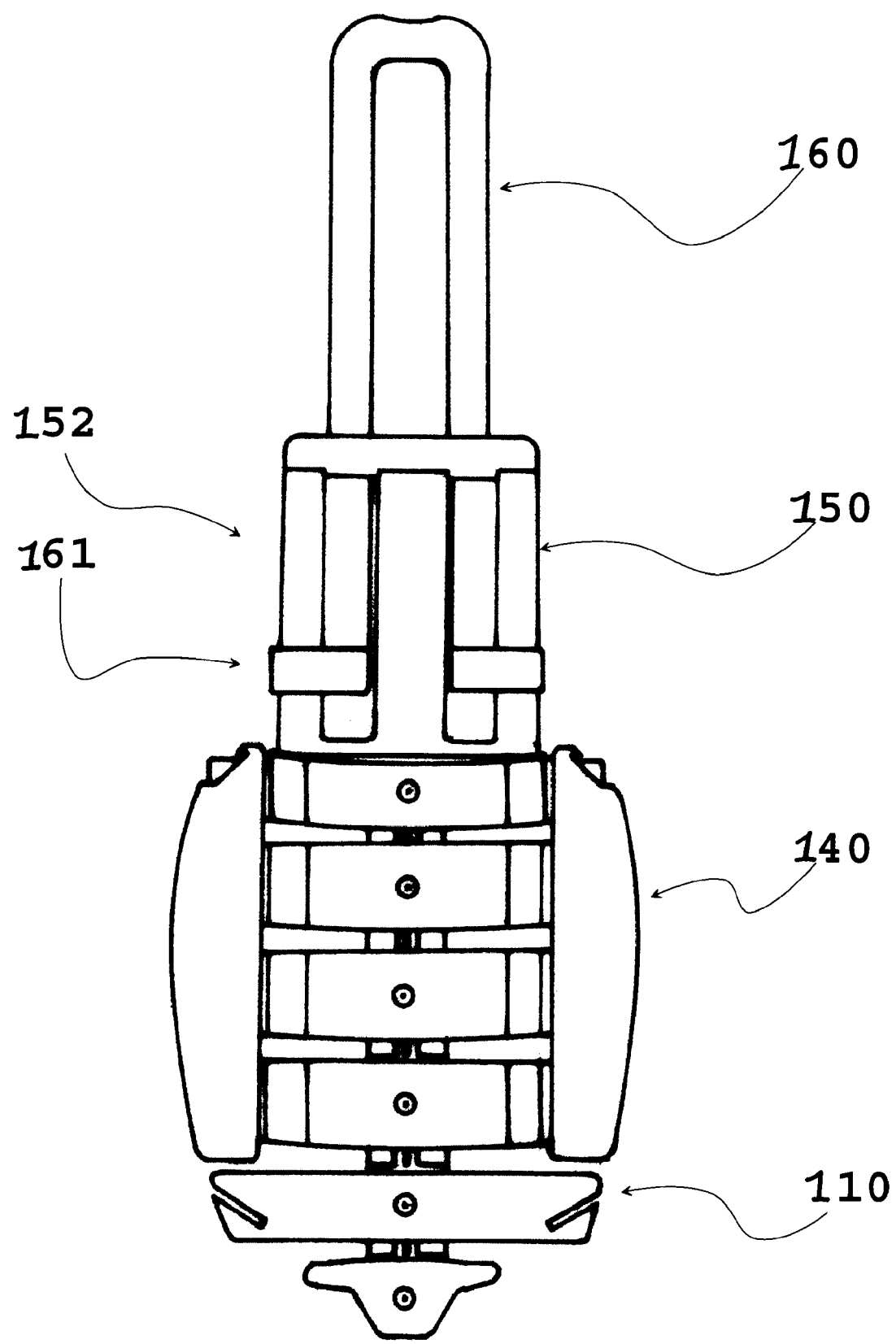
FIG. 20 shows a sectional truss pad with a lumbar extension, a connecting element and a supporting element.

Finally, the thoracic spinal corset 200 is secured cranially to the lower abdominal corset 120 instead of the upper abdominal corset 130 and the supporting structure shown in FIG. 20 is inserted posteriorly into the overall corset consisting of the lower abdominal corset 120 and the thoracic spinal corset 200. In this way, the spinal orthotic device illustrated in FIG. 22 is formed, bridging the spinal area in question from the pelvic ridge up to and including the thorax, relieving stress on the spine, stabilizing and aligning the entire spinal area in the sagittal plane. In the lumbar spine area, the sectional truss pad 110 expanded by the lumbar extension 140 and the stabilized connecting element 150 ensure correction of lordosis. Alignment of the thoracic spine is achieved due to the supporting element 160 used in the upper area and hyperkyphosis is reduced. Likewise, the lumbar lordosis is greatly reduced due to the spinal orthotic device illustrated in FIG. 22 and the thoracic spine is thereby aligned. Because of the modular design, the orthotic device can be scaled back at any time in certain spinal areas by removing the respective supporting elements as improvement occurs, so that a therapeutically correct training effect is achieved. If the complaints exacerbate again subsequently, it is possible to return to the complete spinal orthotic device at any time.

Figure 23:
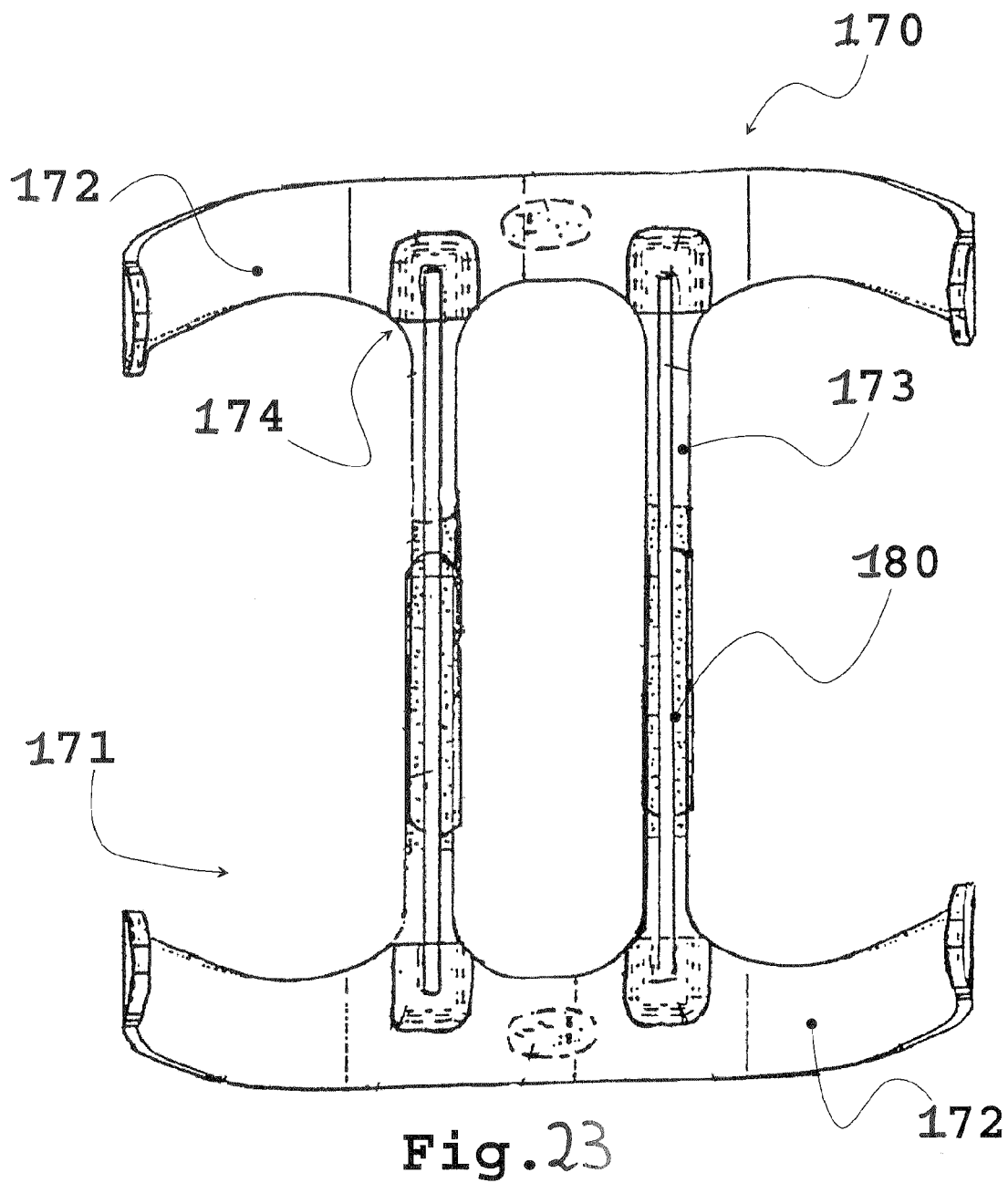
FIG. 23 shows a supporting frame with reinforcing rods.

The complaints caused by osteoporosis in particular require alignment of the spine and stress relief in the sagittal and frontal planes. To this end, the modular system has a bridging frame 170 as illustrated in FIG. 23, connectable into a bandage consisting of the lower and upper abdominal corsets 120 and 130, thus yielding the bridging orthotic device shown in FIG. 24. The bridging frame 170 consists essentially of two II-shaped half elements 171. At its caudal and/or cranial ends, the half elements 171 have a curved carrier 172 that surrounds the lower thorax and/or the pelvis in a supportive manner. Two connecting struts 173 extend away from the carriers 172 along the spine in the direction of the other half element 171. The connecting struts 173 are equipped with VELCRO-type closures and may thus be attached to one another so that the spacing of the carriers 172 can be adapted to the patient's body size. Furthermore, additional reinforcing rods 180 can be attached to the connecting struts 173, so that these rods can be inserted into corresponding pockets 174 on the carriers 172. By inserting the reinforcing rods 180 the stiffness of the bridging frame 170 can be adapted to the particular progress in recovery by the respective patient.

For precision adjustment of the stiffness, different materials such as plastic or metal may be provided for the reinforcing rods 180.

Figure 24:
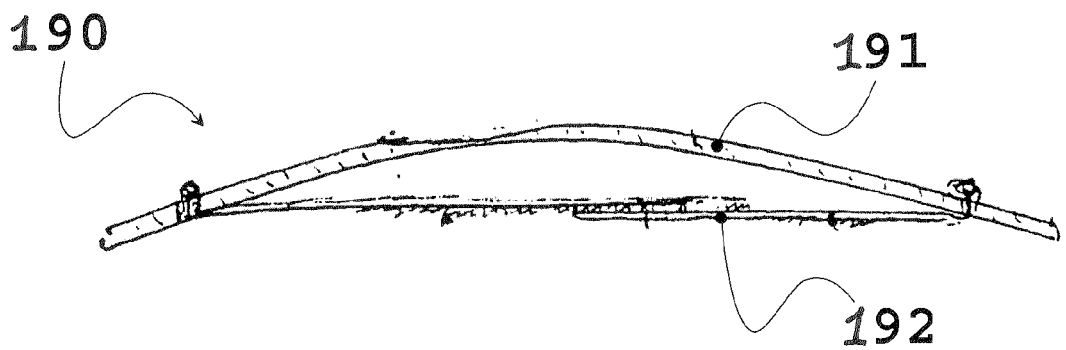
FIG. 24 shows a bridging orthotic device.
Figure 25:
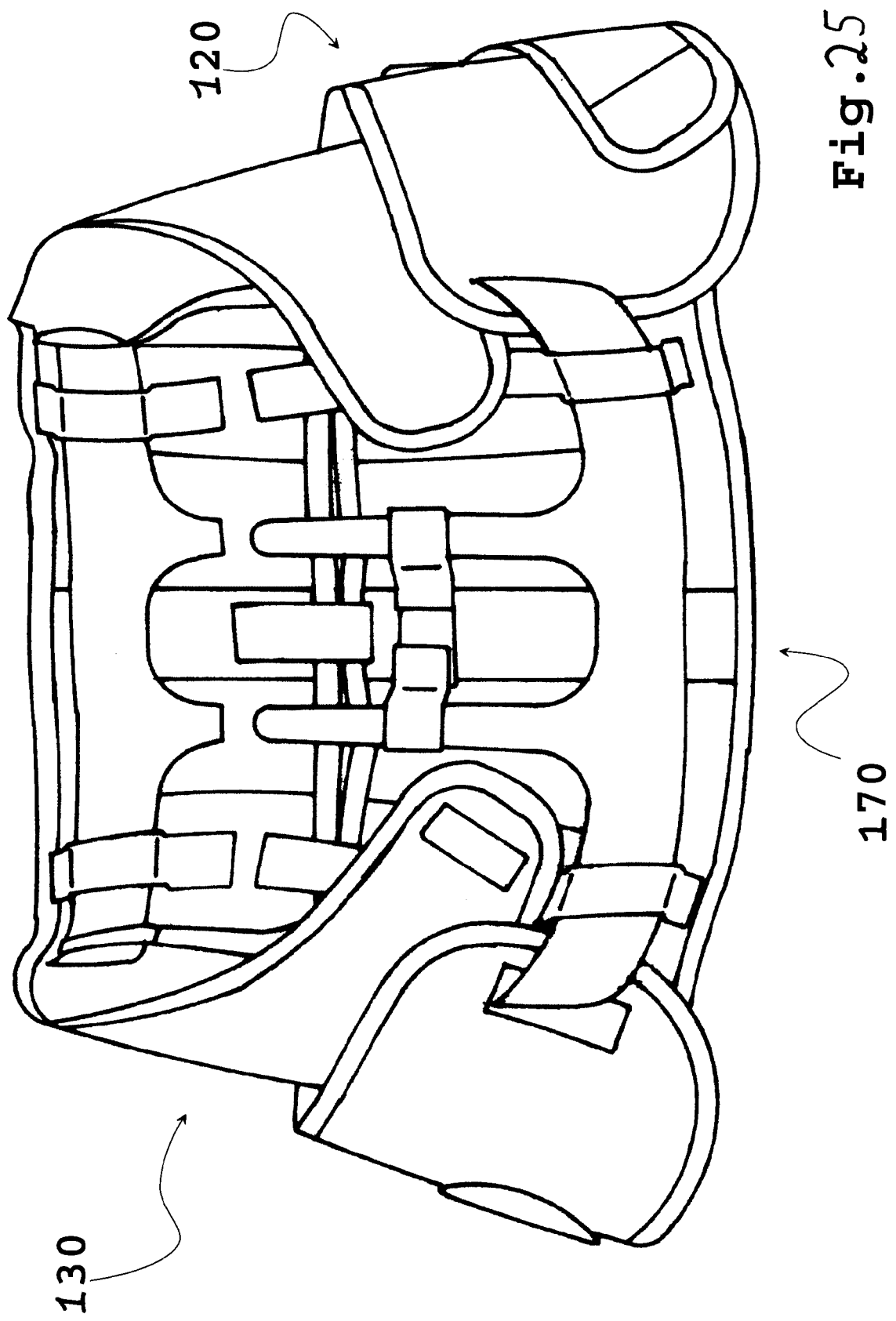
FIG. 25 shows an abdominal truss pad.
Figure 26:
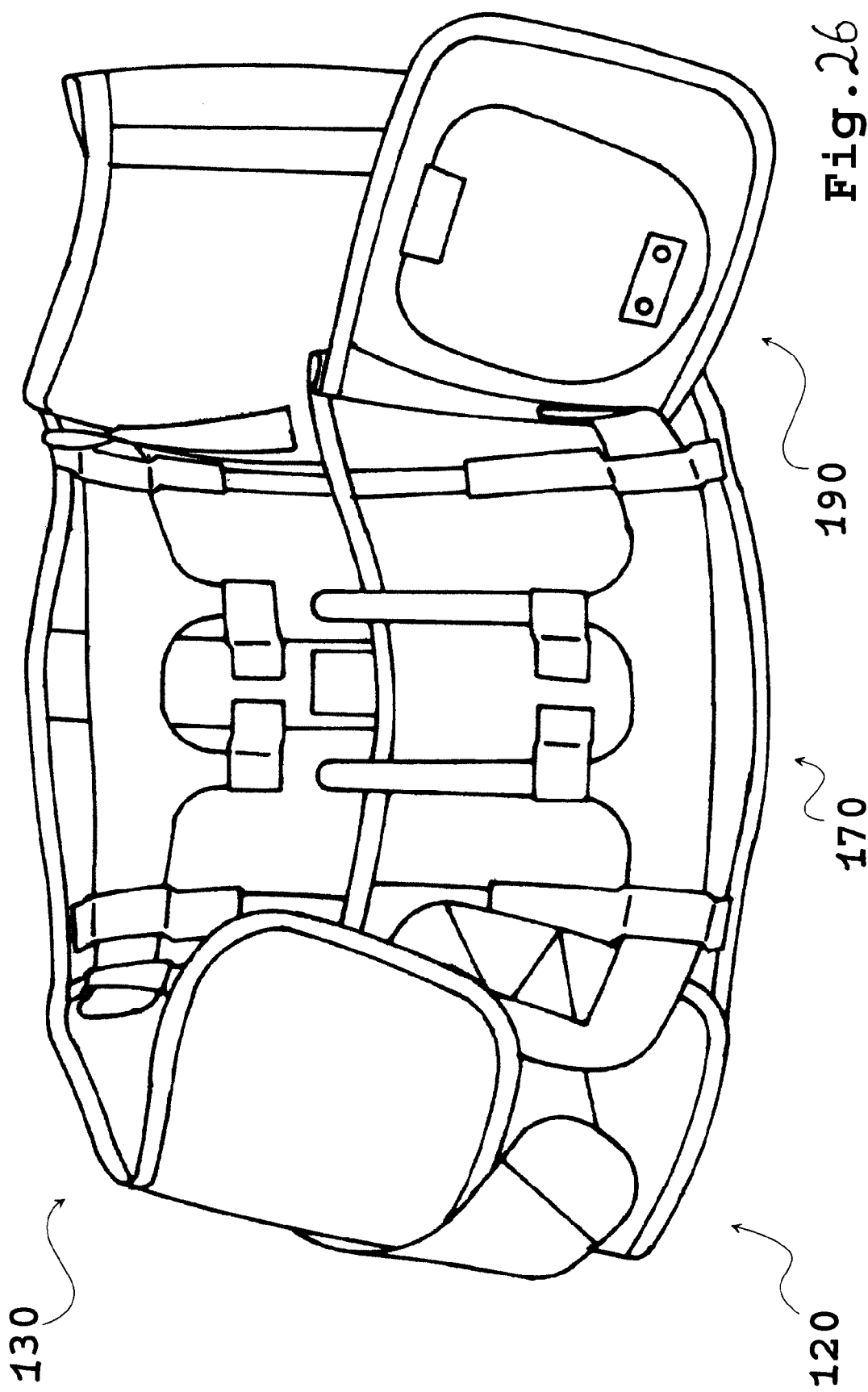
FIG. 26 shows a flexion orthotic device.

To convert the bridging orthotic device shown in FIG. 24 into a flexion orthotic device as shown in FIG. 26, an abdominal truss pad 190, which is shown in a side view in FIG. 25, is secured ventrally in the lower abdominal corset 120. The abdominal truss pad 190 comprises a pressure plate 191, whose concave curvature is adjusted with the help of two strips of a VELCRO-type closure 192. By appropriate prestressing of the VELCRO-type closure 192, the convex profile of the pressure plate 191 is adapted to the desired extent. The entire abdominal truss pad 190 can be secured ventrally in the lower abdominal corset 120 via the VELCRO-type closure 192.

Figure 27:
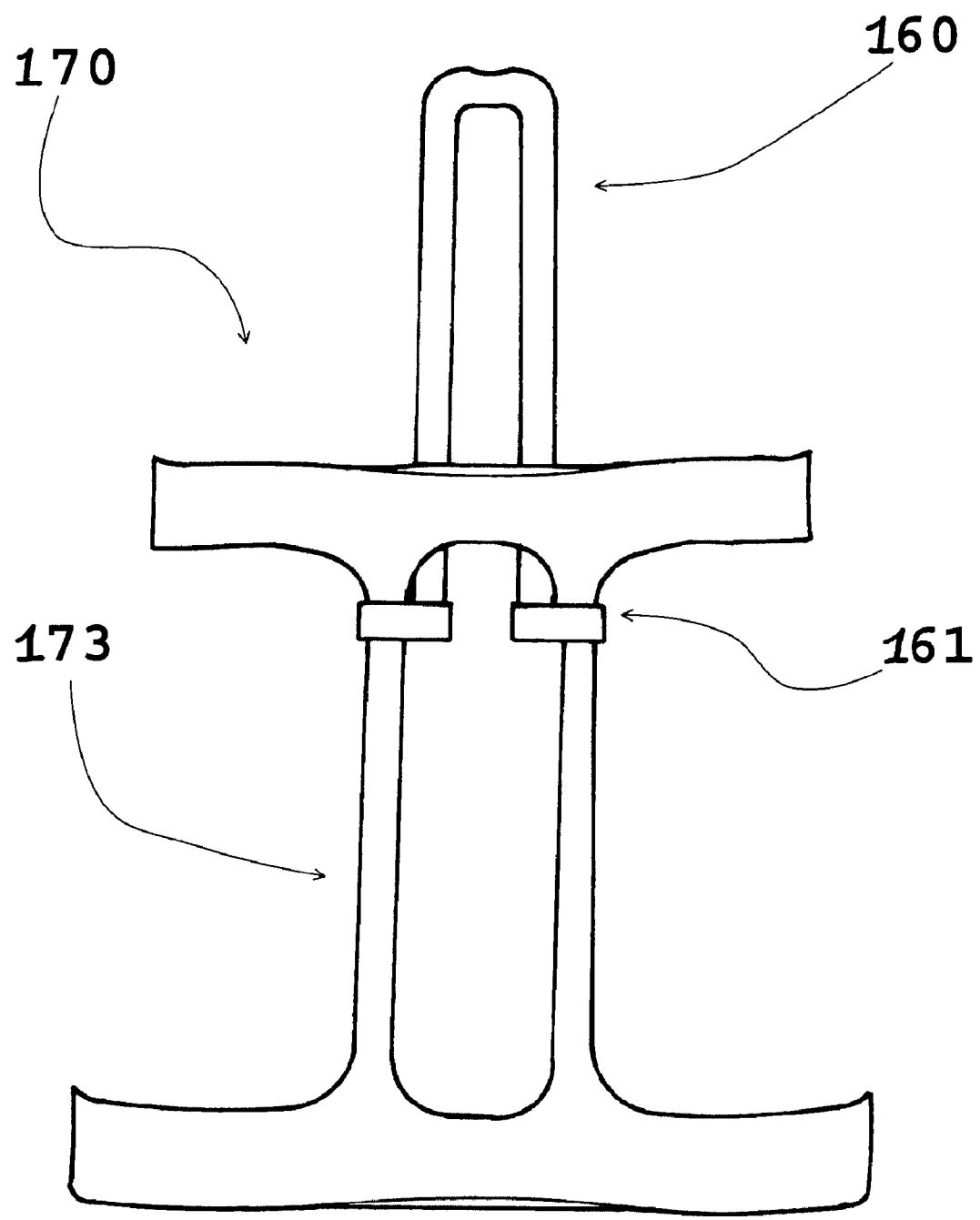
FIG. 27 shows a bridging frame with supporting elements.
Figure 28:
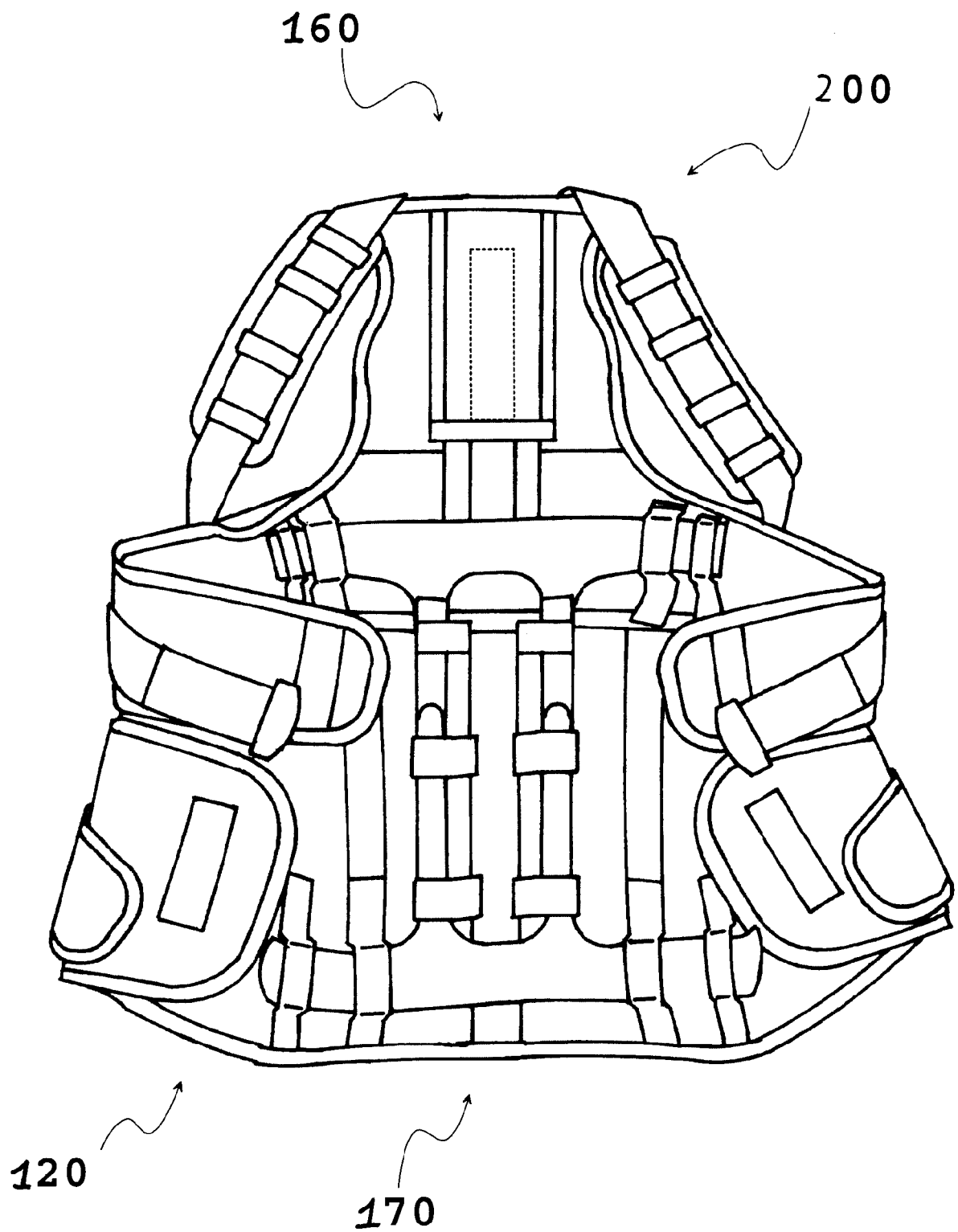
FIG. 28 shows an osteoporosis orthotic device.

With the help of the U-shaped supporting element 160 and the thoracic spinal corset 200, the bridging orthotic device shown in FIG. 24 can be equipped to form an osteoporosis orthotic device as illustrated in FIG. 28, stabilizing and aligning the entire spinal area from the pelvic ridge up to an including the thorax in the sagittal and frontal planes. To do so, the supporting element 160 known from FIG. 18 is attached with its securing clamps 61 to the connecting struts 173 of the frame 170. A height adjustment is possible with no problem through free choice of the connection point. The resulting bandage illustrated in FIG. 27 is attached caudally to the lower abdominal corset 120 and cranially to the thoracic spinal corset 200, which is likewise attached to the lower abdominal corset 120. Furthermore, the supporting element 160 is inserted at its cranial end 162 into the pocket 201 provided for this purpose on the thoracic spinal corset 200, so that ultimately the osteoporosis orthotic device illustrated in FIG. 28 is obtained.

Thanks to the bridging frame 170 which is adjustable in height, this orthotic device ensures a definite lordosis correction which counteracts the compensatory hyperlordosis. An alignment of the thoracic spine is achieved due to the supporting element 160 inserted in the upper area and this greatly reduces the hyperkyphosis. In addition, the lumbar lordosis is definitely corrected and the thoracic spine is aligned. In contrast with other osteoporosis orthotic devices, due to the modular character of the orthotic device configured from this modular system, a later reduction to the particular painful diseased area in question is possible. For example, if relief is achieved in the lumbar area, the lower abdominal corset 120 is removed together with the supporting frame 170 and thereafter only the thoracic spinal corset 200 with the inserted supporting element 160 is worn, as illustrated in FIG. 19. Furthermore, therapeutic corrective training of the spine is possible through various stages of therapy due to the use of initially rigid reinforcing rods 180 on the bridging frame 170 and then later using flexible reinforcing rods. Then if the symptoms are exacerbated again later, a return to the complete spinal orthotic device would be possible at any point in time.

LIST OF REFERENCE NOTATION

10 thoracic orthotic device
11 posterior part
12 strips of cloth
13 shoulder belt system
14 inelastic belt
15 belt holder
16 elastic belt
17 shoulder strap system
18 belt
19 stationary belt end
20 open belt end, e.g., with parts of hook-and-loop fastener (also called VELCRO-type closure parts)
21 pocket
22 hook-and-loop fastener (also called VELCRO-type closure) for pocket
23 supporting element
24 cranial end of the supporting element
25 caudal end of the supporting element
26 recess in the supporting element
27 curve (around the spine) in the supporting element
28 coupling element
29 fastening tabs
30 adapter part
31 receptacle area for 23
32 receptacle area for 41
33 recess in the adapter part
34 VELCRO-type closure holder
35 guide strap
36 pull-through strap
37 sewed-on tab
38 rounded corner
40 lumbar spine corset
41 corset supporting element
42 cranial end of corset supporting element
43 caudal end of corset supporting element
44 recess in corset supporting element
45 curve (around spine) in the corset supporting element
46 receptacle area and/or passage
47 curve-supporting clasp
48 counter-coupling member
50 spinal orthotic device
60 thoracolumbar orthotic device
110 sectional truss pad
111 sections joined together with an articulation
112 contact surface
113 contacting insertion ends
114 joints
115 fixation element
120 lower abdominal corset
130 upper abdominal corset
140 lumbar extension
141 sections
142 supporting rail
150 contacting element
151 recess
152 fork-like receptacle
160 supporting element
161 securing clamp
162 cranial end
170 bridging frame
171 half elements
172 curved carriers
173 connecting struts
174 pockets
180 reinforcing rods
190 abdominal truss pad
191 pressure plate
192 VELCRO-type tape
200 thoracic spinal corset
201 pocket
L1 lumbar vertebra 1
L2 lumbar vertebra 2
L3 lumbar vertebra 3
L4 lumbar vertebra 4
L5 lumbar vertebra 5
S1 first sacral vertebra

What is claimed is:

1. A spinal orthotic device, configured from one or more elements of a modular system comprising the following elements:
    a1) a lower abdominal corset,
    b1) an upper abdominal corset that can be attached cranially to the lower abdominal corset,
    c1) a corset supporting element that can be secured posteriorly in the lower abdominal corset and is arranged along the lumbar spine, supporting the spine while restricting sagittal mobility,
    e1) a thoracic spinal corset that can be attached cranially to the lower abdominal corset,
    g1) at least one curved supporting clasp that can be inserted posteriorly optionally into a bandage of the lower abdominal corset and the upper abdominal corset or into a bandage of the lower abdominal corset and the thoracic spinal corset, said curved supporting clasp on the corset supporting element being used for correction of lordosis and for restriction of sagittal and frontal mobility in the area of the lumbar spine,
    h1) at least one supporting element which can optionally be secured cranially in the thoracic spinal corset and caudally to the corset supporting element and extends laterally along the spine to align and relieve the spine in the sagittal plane,
    i1) and an abdominal truss pad that can be attached ventrally to the lower abdominal corset for correction of lordosis of the lumbar spine and increasing the intra-abdominal pressure.

2. The spinal orthotic device according to claim 1, characterized in that the supporting element has a coupling member and the corset supporting element has a counter-coupling member which can be joined together in particular via a form-fitting connection.

3. The spinal orthotic device according to claim 1 or 2, characterized in that the thoracic spinal corset has a shoulder belt system with which a posterior part, in particular having a large area, can be held like a backpack and a ventral shoulder strap system which is also connected to the posterior part.

4. The spinal orthotic device according to claim 3, characterized in that the shoulder belt system has inelastic belts which have a synthetic textile in particular.

5. The spinal orthotic device according to claim 4, characterized in that the shoulder belt system is arranged on the posterior part via belt holders, whereby the belt holders are undetachably attached to the posterior part, in particular via elastic belts.

6. The spinal orthotic device according to claim 3, characterized in that the shoulder belt system is arranged on the posterior part via belt holders, whereby the belt holders are undetachably attached to the posterior part, in particular via elastic belts.

7. The spinal orthotic device according to claim 1 or 2, characterized in that a shoulder strap system and/or the upper abdominal corset can be reversibly attached to the posterior part by means of fastening tabs.

8. The spinal orthotic device according to claim 7, characterized in that the fastening tabs are designed with double walls, whereby the insides are provided with hook-and-loop fasteners which cooperate with suitably designed stationary belt ends of the shoulder strap system so that the shoulder strap system is held reversibly on the posterior part.

9. The thoracic spinal orthotic device according to claim 1 or 2, characterized in that one supporting element is arranged at least partially in a pocket on the posterior part.

10. The spinal orthotic device according to claim 1 or 2, characterized in that the coupling member and the counter-coupling member connect the thoracic spinal corset to the lower abdominal corset and/or to the upper abdominal corset.

11. A spinal orthotic device, configured from one or more elements of the modular system comprising the following elements:
   a2) a lower abdominal corset,
   b2) an upper abdominal corset that can be attached cranially to the lower abdominal corset,
   c2) a basic truss pad as a corset supporting element that can be attached posteriorly to the lower abdominal corset and is arranged along the lumbar spine and supports the third to fifth lumbar vertebrae and the first sacral vertebra with a restriction on sagittal mobility,
   d2) a lumbar extension that is connectable to the basic truss pad and expands the basic truss pad, such that a bandage comprising the basic truss pad and the lumbar extension supports the first to fifth lumbar vertebrae and the first sacral vertebra with a restriction of sagittal mobility, e2) a thoracic spinal corset that can be attached cranially to the lower abdominal corset, f2) a connecting element that can be attached to the basic truss pad, g2) a bridging frame that can be inserted posteriorly optionally into a bandage comprising the lower abdominal corset and the upper abdominal corset or into a bandage comprising the lower abdominal corset and the thoracic spinal corset; it has a lordosis correcting effect and restricts sagittal and frontal mobility in the lumbar spinal area, h2) an essentially U-shaped supporting element that can be attached cranially to the thoracic spinal corset and caudally optionally to the bridging frame or to the connecting element, the legs thereof extending on both sides along the spine to align and relieve the spine in the sagittal plane, i2) and an abdominal truss pad that can be attached ventrally in the lower abdominal corset for correction of lordosis of the lumbar spine and to increase the intra-abdominal pressure.

12. The spinal orthotic device according to claim 11, characterized in that the basic truss pad is a sectional truss pad comprising four sections that can be connected together with an articulated joint and are arranged along the lumbar spine and bridge transversely the third to fifth lumbar vertebrae as well as the first sacral vertebra.

13. The spinal orthotic device according to claim 12, characterized in that the modular system comprises a fixation element that can be attached posteriorly to the sectional truss pad such that sections of the sectional truss pad are fixed immovably in the sagittal plane in relation to one another.

14. The spinal orthotic device according to claim 12 or 13, characterized in that the lumbar extension contains two sections that can be joined together with an articulation for the sectional truss pad and two supporting rails whereby the sections of the lumbar extension can be inserted into the sectional truss pad in such a way that the sections of the truss pad that has been extended by including the lumbar extension bridge the first to fifth lumbar vertebrae as well as the first sacral vertebra and whereby the supporting rails can be attached laterally to the sectional truss pad in such a way that at least the sections which bridge the first four lumbar vertebrae are immovably fixed in relation to one another.

15. The spinal orthotic device according to claim 14, characterized in that the modular system comprises reinforcing rods that can be attached to the bridging frame to adjust the stiffness of the bridging frame.

16. The spinal orthotic device according to claim 13, characterized in that the modular system comprises reinforcing rods that can be attached to the bridging frame to adjust the stiffness of the bridging frame.

17. The spinal orthotic device according to claim 11 or 12, characterized in that the modular system comprises reinforcing rods that can be attached to the bridging frame to adjust the stiffness of the bridging frame.

18. The spinal orthotic device according to claims 11 or 12, characterized in that the bridging frame has a curved supporting clasp, especially on the cranial and caudal ends.

* * * * *